(12) United States Patent
Mochizuki

(10) Patent No.: US 10,532,143 B2
(45) Date of Patent: Jan. 14, 2020

(54) INSTALLATION MEMBER AND PERISTALTIC PUMP

(71) Applicant: Nikkiso Company Limited, Tokyo (JP)

(72) Inventor: Hiroaki Mochizuki, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 157 days.

(21) Appl. No.: 15/292,404

(22) Filed: Oct. 13, 2016

(65) Prior Publication Data

US 2017/0028117 A1 Feb. 2, 2017

Related U.S. Application Data

(63) Continuation of application No. PCT/JP2015/061583, filed on Apr. 15, 2015.

(30) Foreign Application Priority Data

Apr. 15, 2014 (JP) .................................. 2014-083723

(51) Int. Cl.
*A61M 1/26* (2006.01)
*F04B 43/12* (2006.01)
(Continued)

(52) U.S. Cl.
CPC .......... *A61M 1/267* (2014.02); *A61M 1/3638* (2014.02); *A61M 5/14232* (2013.01);
(Continued)

(58) Field of Classification Search
CPC ...... F04B 13/00; F04B 43/08; F04B 43/1253; F04B 43/1269; A61M 1/267;
(Continued)

(56) References Cited

U.S. PATENT DOCUMENTS 3,046,788 A   7/1962 Laimin
4,090,404 A   5/1978 Dupont
(Continued)

FOREIGN PATENT DOCUMENTS

CN   1405450 A   3/2003
EP   1666078     6/2006
(Continued)

OTHER PUBLICATIONS

International Search Report from the Japanese Patent Office for Application No. PCT/JP2015/061583, dated Jul. 7, 2015.
(Continued)

*Primary Examiner* — Dominick L Plakkoottam
*Assistant Examiner* — Connor J Tremarche
(74) *Attorney, Agent, or Firm* — Young Basile Hanlon & MacFarlane, P.C.

(57) ABSTRACT

An installation member and a peristaltic pump are provided that allow work of attachment and work of detachment of a flexible tube to be peristaltic to and from a stator to be performed more easily and smoothly. An installation member that is to be detachably attached to a peristaltic pump including: a stator including an attachment recessed portion, in which a flexible tube to be peristaltic, is attached; a rotor that is rotatably driven in the attachment recessed portion; and a roller that causes the fluid to flow by imparting peristaltic motion to the flexible tube to be peristaltic attached to the attachment recessed portion in a longitudinal direction in association with rotation of the rotor while compressing the flexible tube to be peristaltic in a radial direction. The installation member including: a main body that is attachable to a predetermined portion of the stator, and that is formed integrally with a downstream-side fixing portion of the flexible tube to be peristaltic; and a notch (Continued)

portion that allows an upstream-side fixing portion of the flexible tube to be peristaltic to be positioned.

20 Claims, 15 Drawing Sheets

(51) Int. Cl.
*A61M 1/36* (2006.01)
*A61M 5/142* (2006.01)
*A61M 1/10* (2006.01)
*F04B 43/08* (2006.01)

(52) U.S. Cl.
CPC ....... *F04B 43/1253* (2013.01); *A61M 1/1006* (2014.02); *A61M 1/1012* (2014.02); *A61M 1/1039* (2014.02); *F04B 43/08* (2013.01)

(58) Field of Classification Search
CPC .. A61M 1/3638; A61M 1/006; A61M 1/1012; A61M 1/1039; A61M 5/3638; A61M 5/14232
USPC ..................................................... 417/477.3
See application file for complete search history.

(56) References Cited

U.S. PATENT DOCUMENTS

| | | | |
|---|---|---|---|
| 4,460,355 A | 7/1984 | Layman | |
| 4,498,843 A | 2/1985 | Schneider et al. | |
| 4,534,756 A | 8/1985 | Nelson | |
| 4,558,996 A | 12/1985 | Becker | |
| 4,585,399 A | 4/1986 | Baier | |
| 4,743,228 A | 5/1988 | Butterfield | |
| 4,762,518 A | 8/1988 | Kreinick | |
| 4,784,576 A | 11/1988 | Bloom | |
| 4,969,808 A | 11/1990 | Tsukada | |
| 5,024,099 A | 6/1991 | Lee | |
| 5,215,450 A | 6/1993 | Tamari | |
| 5,336,051 A | 8/1994 | Tamari | |
| 5,356,378 A | 10/1994 | Doan | |
| 5,380,172 A | 1/1995 | Ulbing | |
| 5,429,483 A | 7/1995 | Tamari | |
| 5,501,665 A | 3/1996 | Jhuboo et al. | |
| 5,577,891 A * | 11/1996 | Loughnane | F04B 43/082 417/412 |
| 5,720,721 A | 2/1998 | Dumas et al. | |
| 5,813,842 A | 9/1998 | Tamari | |
| 5,814,004 A | 9/1998 | Tamari | |
| 5,827,223 A | 10/1998 | Butterfield | |
| 5,920,054 A | 7/1999 | Uber | |
| 5,927,951 A | 7/1999 | Tamari | |
| 6,039,078 A | 3/2000 | Tamari | |
| 6,374,084 B1 | 4/2002 | Fok | |
| 6,423,029 B1 | 7/2002 | Elsberry | |
| 6,497,680 B1 | 12/2002 | Holst | |
| 6,868,720 B2 | 3/2005 | Lobdell | |
| 7,004,924 B1 | 2/2006 | Brugger et al. | |
| 7,037,092 B2 | 5/2006 | Kagawa et al. | |
| 7,462,163 B2 | 12/2008 | Yap et al. | |
| 7,935,912 B2 | 5/2011 | Arima | |
| 8,011,905 B2 | 9/2011 | Artsyukhovich | |
| 9,004,886 B2 | 4/2015 | Beck | |
| 9,662,433 B2 | 5/2017 | Matsu | |
| 2001/0004444 A1 | 6/2001 | Haser | |
| 2002/0151838 A1 | 10/2002 | Beck et al. | |
| 2003/0040700 A1 | 2/2003 | Hickle et al. | |
| 2003/0071072 A1 | 4/2003 | Takahashi et al. | |
| 2003/0214412 A1 | 11/2003 | Ho | |
| 2005/0025647 A1 | 2/2005 | Ortega et al. | |
| 2007/0217933 A1 | 9/2007 | Haser et al. | |
| 2007/0258838 A1 * | 11/2007 | Drake | F04B 43/0072 417/477.11 |
| 2008/0154095 A1 | 6/2008 | Stubkjaer | |
| 2009/0214365 A1 * | 8/2009 | Norman | A61M 5/14232 417/474 |
| 2010/0049134 A1 | 2/2010 | Schuman, Jr. | |
| 2010/0106466 A1 | 4/2010 | Frohlich | |
| 2010/0203179 A1 | 8/2010 | Kaushik | |
| 2011/0033318 A1 | 2/2011 | Ramirez, Jr. et al. | |
| 2011/0130741 A1 | 6/2011 | Miles | |
| 2011/0230814 A1 | 9/2011 | Kopperschmidt et al. | |
| 2012/0082576 A1 | 4/2012 | Beck | |
| 2012/0083737 A1 | 4/2012 | Beck | |
| 2014/0219829 A1 | 8/2014 | Matsuo et al. | |
| 2015/0217040 A1 | 8/2015 | Matsuo et al. | |
| 2015/0238677 A1 | 8/2015 | Akita et al. | |
| 2018/0133384 A1 | 5/2018 | Tokunaga et al. | |

FOREIGN PATENT DOCUMENTS

| | | | |
|---|---|---|---|
| EP | 1947340 A1 | 7/2008 | |
| EP | 2749858 | 7/2014 | |
| JP | S56-113083 A | 9/1981 | |
| JP | S64-022357 | 2/1989 | |
| JP | H03-001290 | 1/1991 | |
| JP | H03-001290 U1 | 1/1991 | |
| JP | H04-015938 | 2/1992 | |
| JP | H04-015938 U1 | 2/1992 | |
| JP | H08-510812 | 11/1996 | |
| JP | H8-510812 A | 11/1996 | |
| JP | 2003-265601 A | 9/2003 | |
| JP | 2004-049494 | 2/2004 | |
| JP | 2004-049494 A | 2/2004 | |
| JP | 2004-187990 | 7/2004 | |
| JP | 2004-187990 A | 7/2004 | |
| JP | 2005-503202 A | 2/2005 | |
| JP | 2007-224909 A | 9/2007 | |
| JP | 2008-000425 A | 1/2008 | |
| JP | 2008-002388 A | 1/2008 | |
| JP | 2008000425 A * | 1/2008 | |
| JP | 2008-208808 | 9/2008 | |
| JP | 2008-208808 A | 9/2008 | |
| JP | 2008-289635 A | 12/2008 | |
| JP | 2009-525770 | 7/2009 | |
| JP | 2009-525770 A | 7/2009 | |
| JP | 2009/297193 A | 12/2009 | |
| JP | 2010-188170 A | 9/2010 | |
| JP | 2010-190062 A | 9/2010 | |
| JP | 2010190062 A * | 9/2010 | ......... F04B 43/1261 |
| JP | 2011-030880 A | 2/2011 | |
| JP | 2012-192100 A | 10/2012 | |
| WO | 1994/028309 A1 | 8/1994 | |
| WO | 1994/028309 A1 | 12/1994 | |
| WO | 95/10310 A1 | 4/1995 | |
| WO | 97/10013 A1 | 3/1997 | |
| WO | 1997/010013 | 3/1997 | |
| WO | 2007/093064 A1 | 8/2007 | |
| WO | 2007-093064 A1 | 8/2007 | |
| WO | 2010/020380 A | 2/2010 | |

OTHER PUBLICATIONS

Written Opinion from the Japanese Patent Office for Application No. PCT/JP2015/061583, dated Jul. 7, 2015.
Potentially related application, U.S. Appl. No. 14/688,064, dated Apr. 16, 2015, publication No. 2015/0217040, dated, Aug. 6, 2015.
Potentially related application, U.S. Appl. No. 14/688,068, dated Apr. 16, 2015, publication No. 2015/0238677, dated, Aug. 27, 2015.
Extended European Search Report, Application No. 15779984.2 dated Nov. 24, 2017.
Supplementary European Search Report dated May 27, 2016 for Application No. PCT/JP2013/078272.
International Search Report, Application No. PCT/JP2013/078272, dated Jan. 21, 2014.
International Search Report, Application No. PCT/JP2013/078271, dated Jan. 21, 2014.
Potentially Related Patent Application, U.S. Appl. No. 14/186,193, published as 2014/0219829, published on Aug. 7, 2014.
Translation of International Search Report, Application No. PCT/JP2012/070614, dated Sep. 11, 2012.

(56) References Cited

OTHER PUBLICATIONS

Extended European Search Report dated Apr. 8, 2015 for Application No. 12826289.

* cited by examiner

[FIG 1]
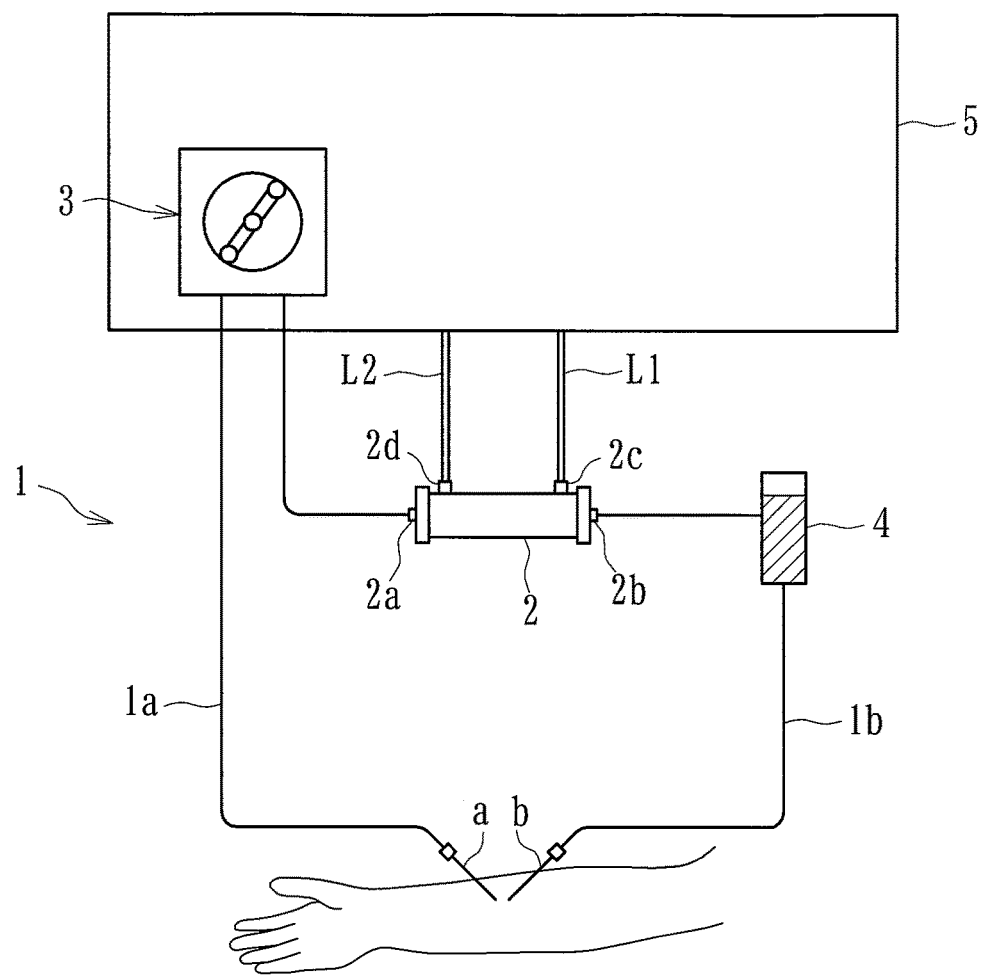
[FIG 2]
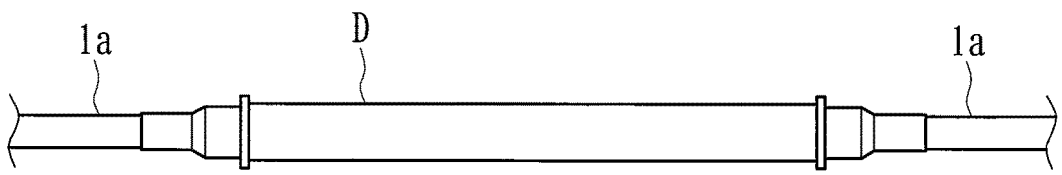

[FIG 3]
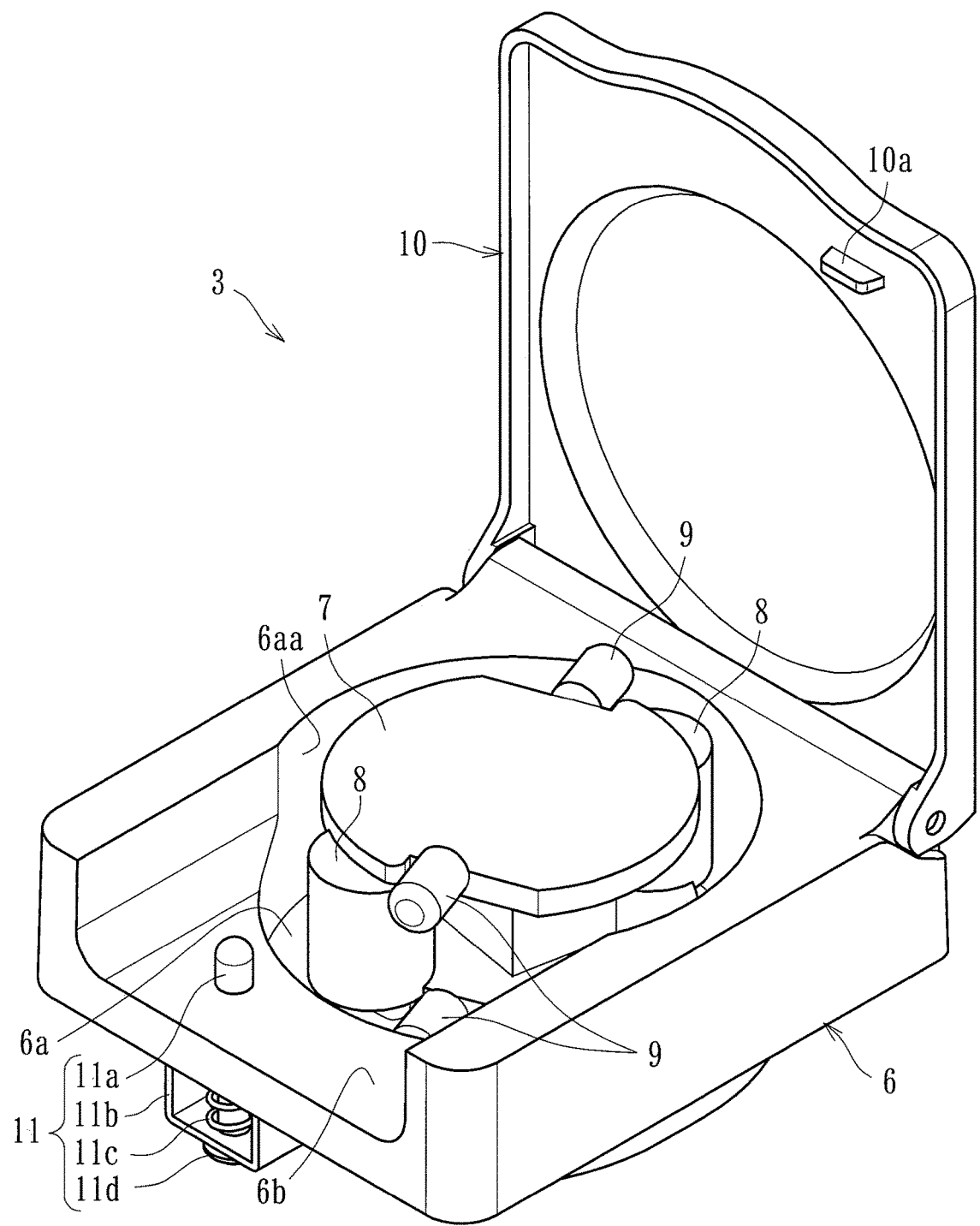

[FIG 4]
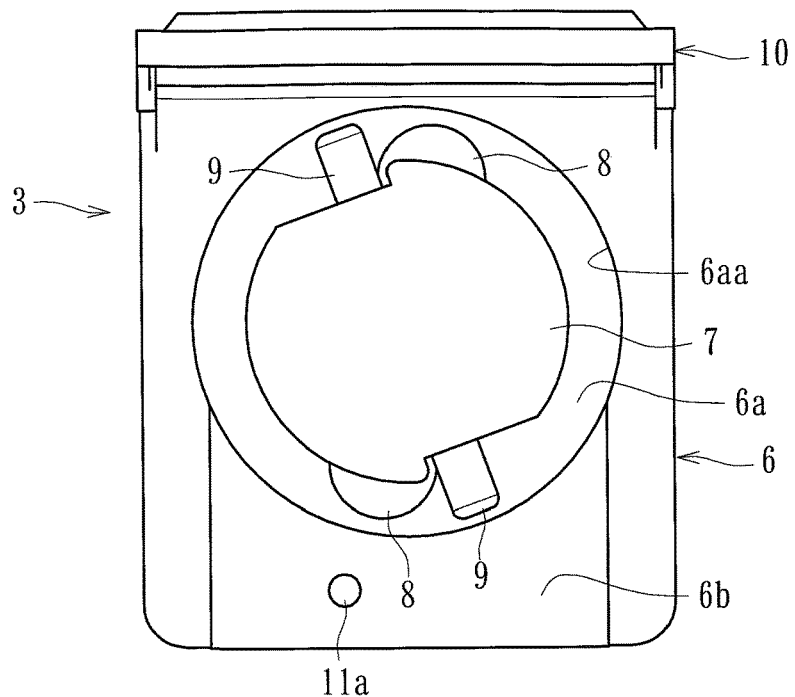
[FIG 5]
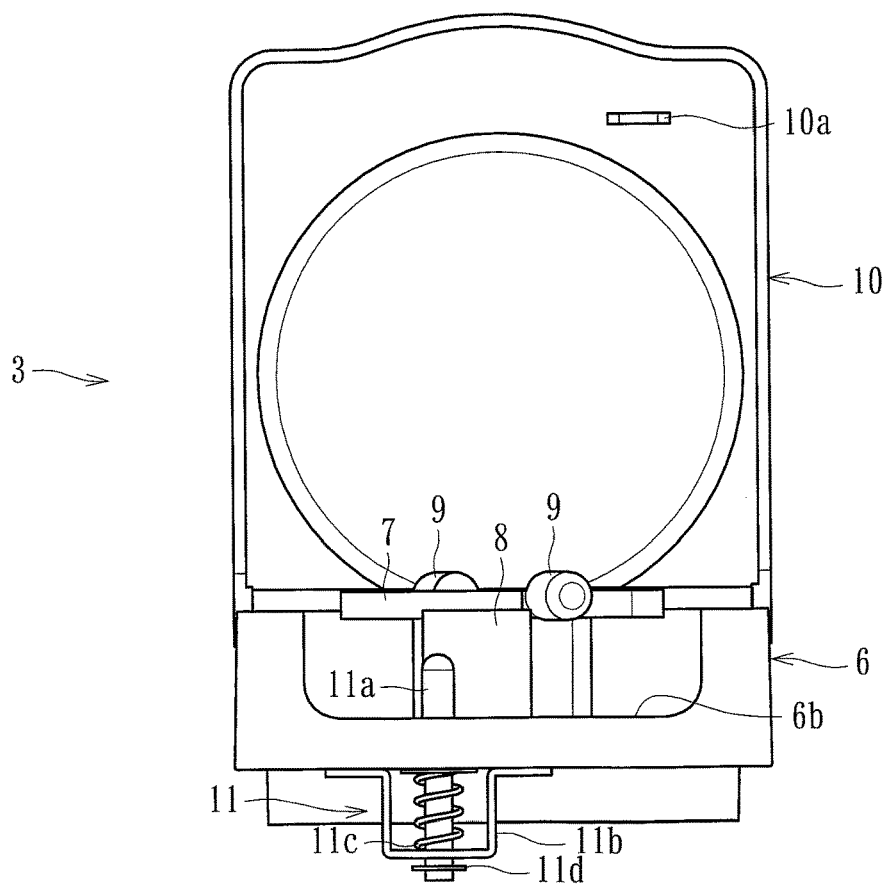

[FIG 6]
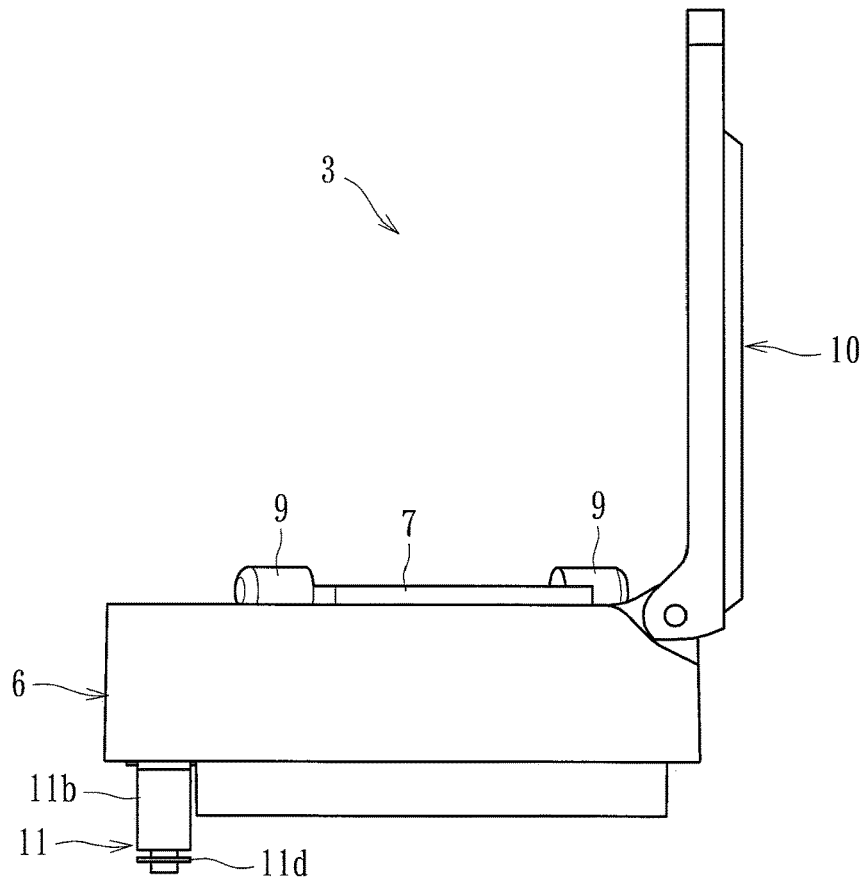
[FIG 7]
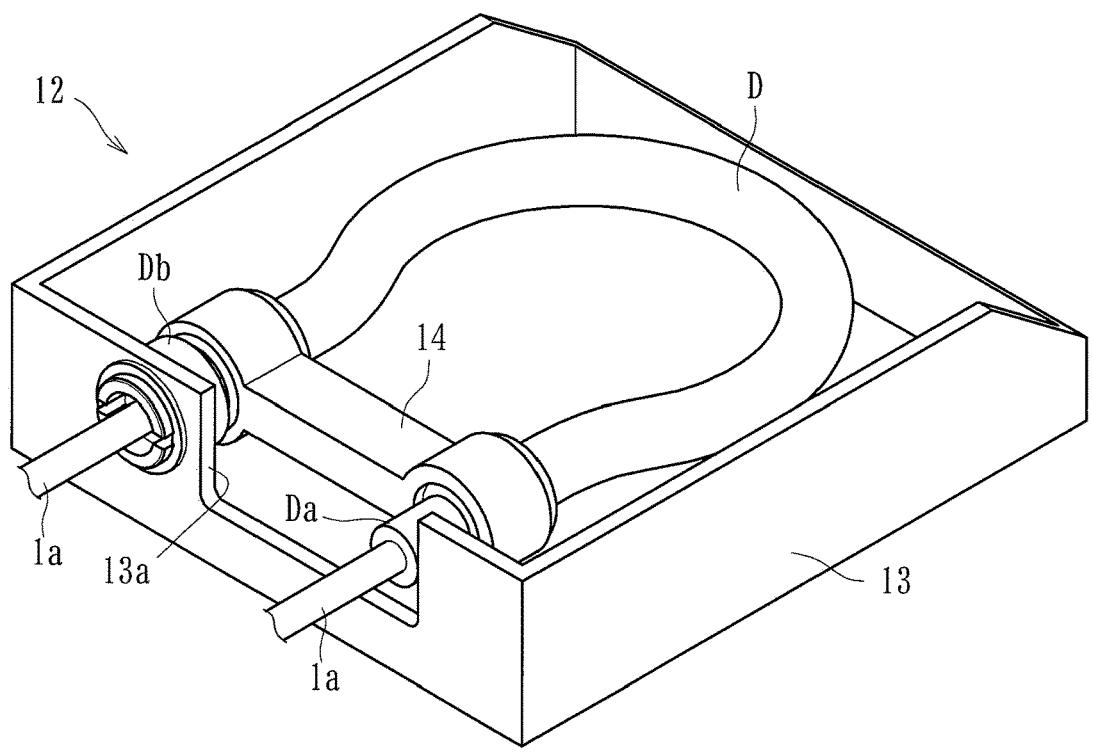

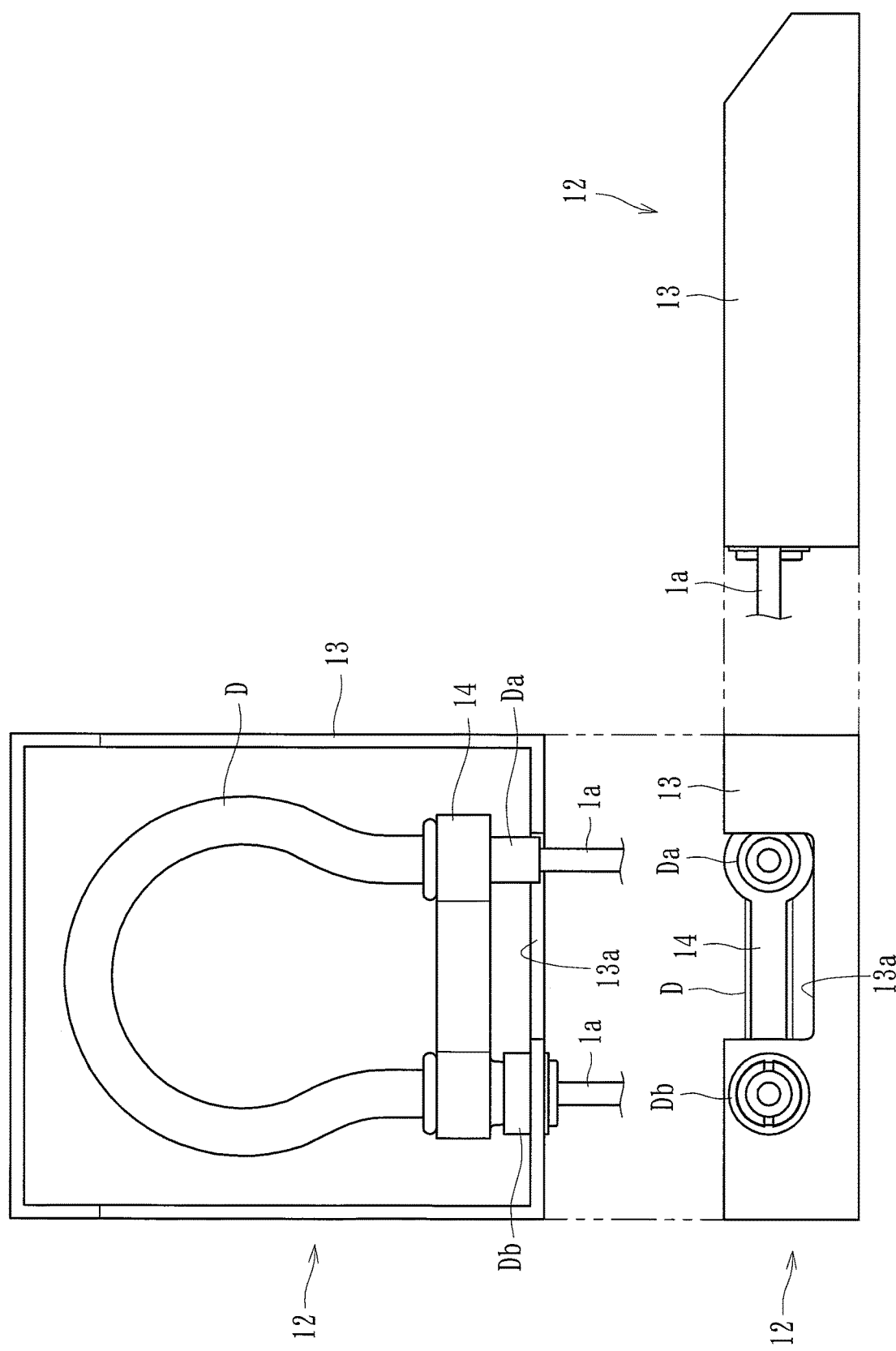

[FIG 9]
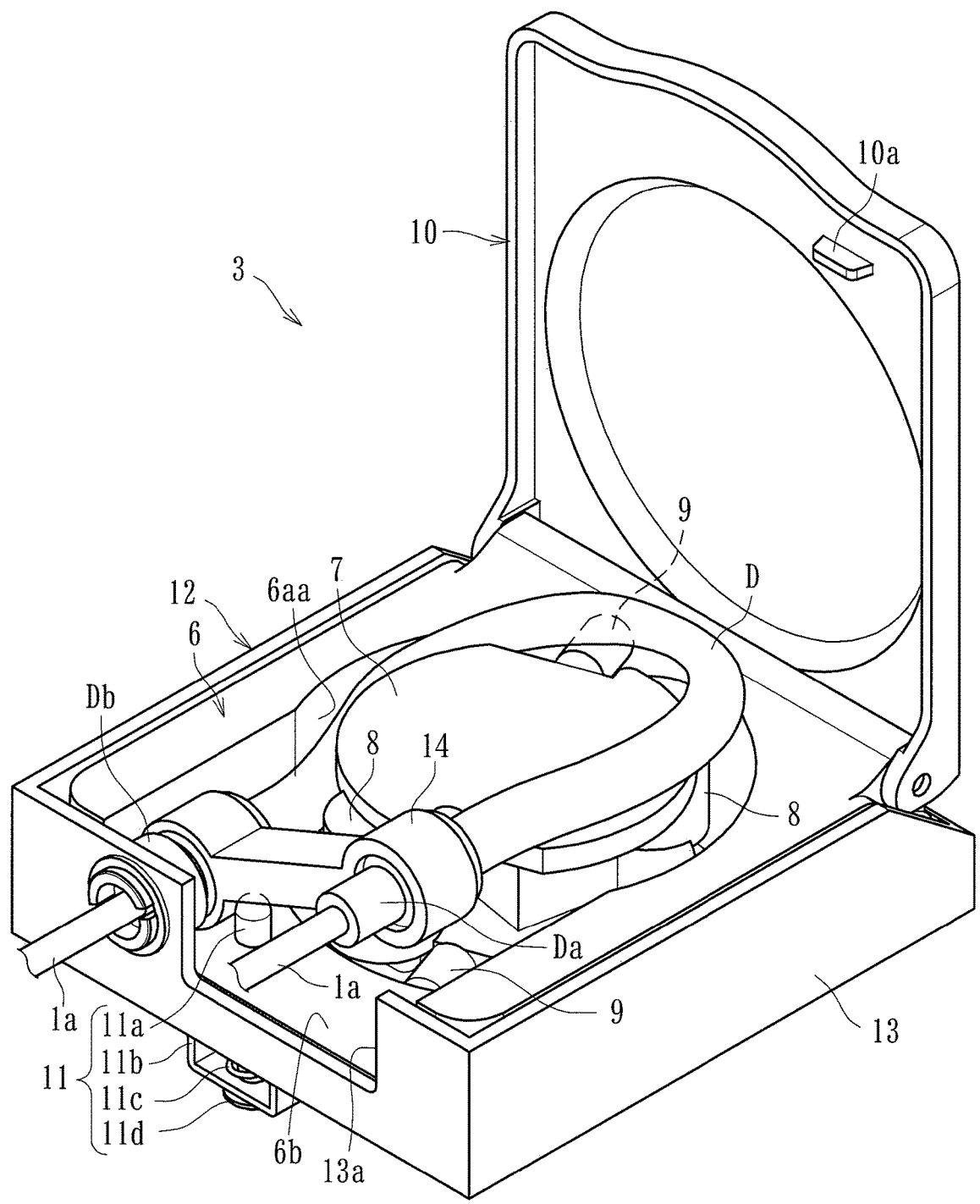

[FIG 10]
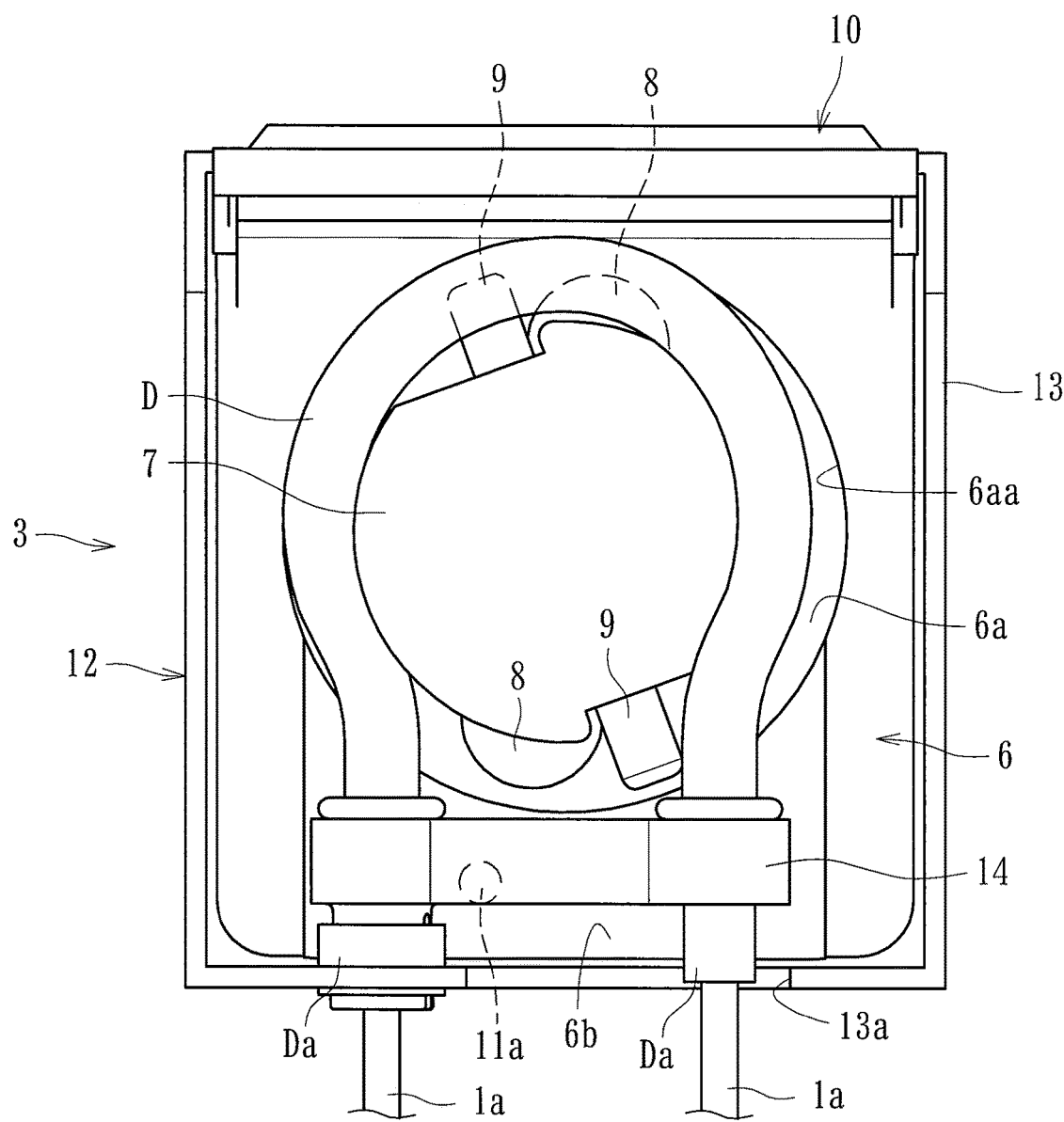

[FIG 11]
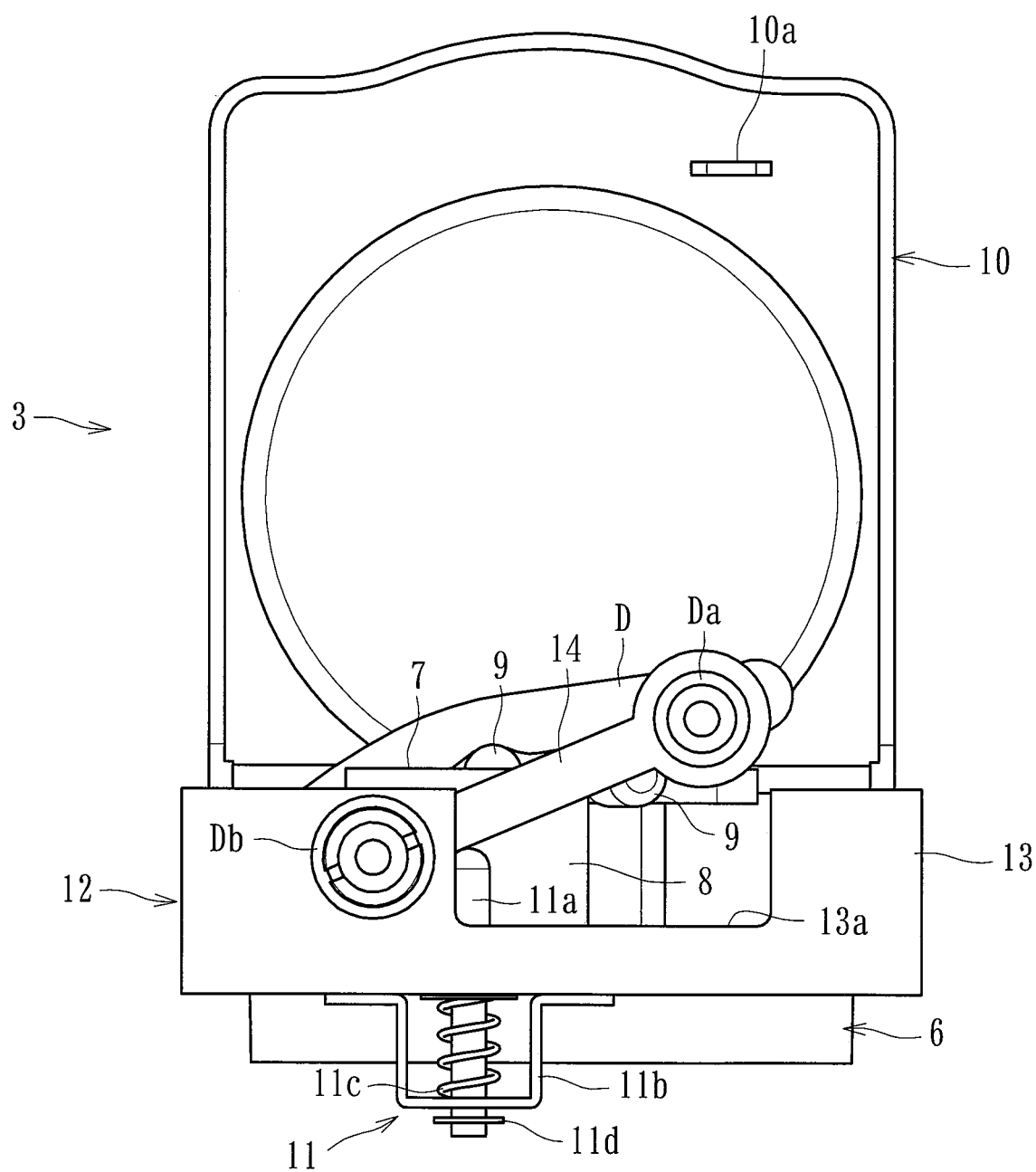

[FIG 12]
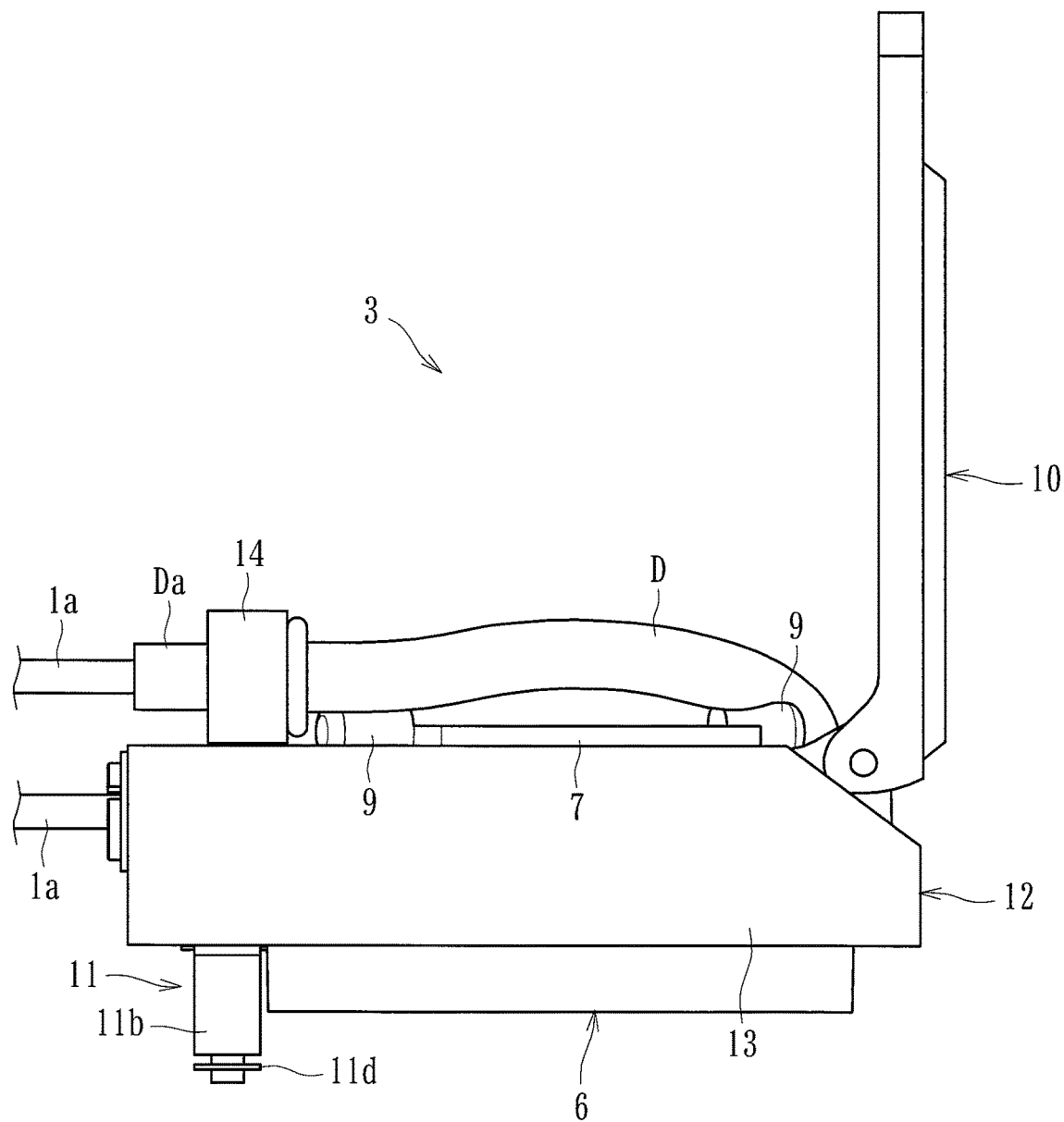

[FIG 13]
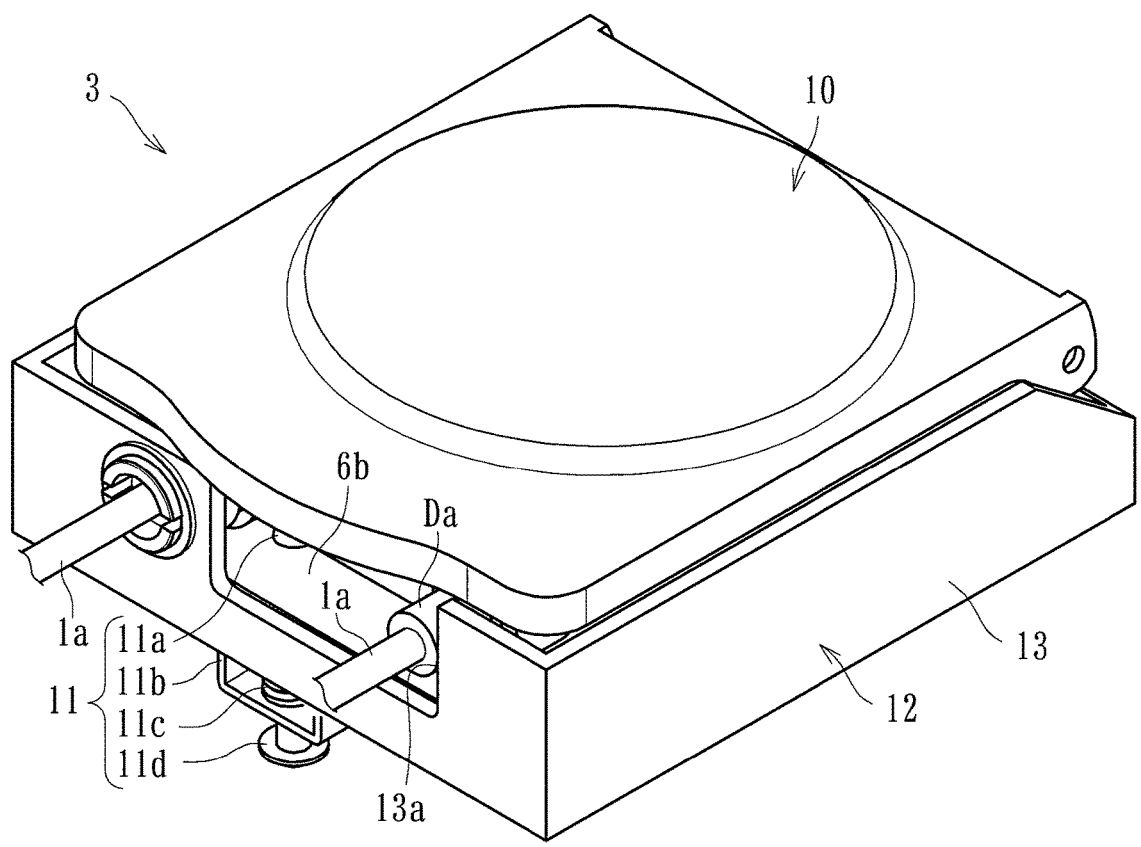

[FIG 14]
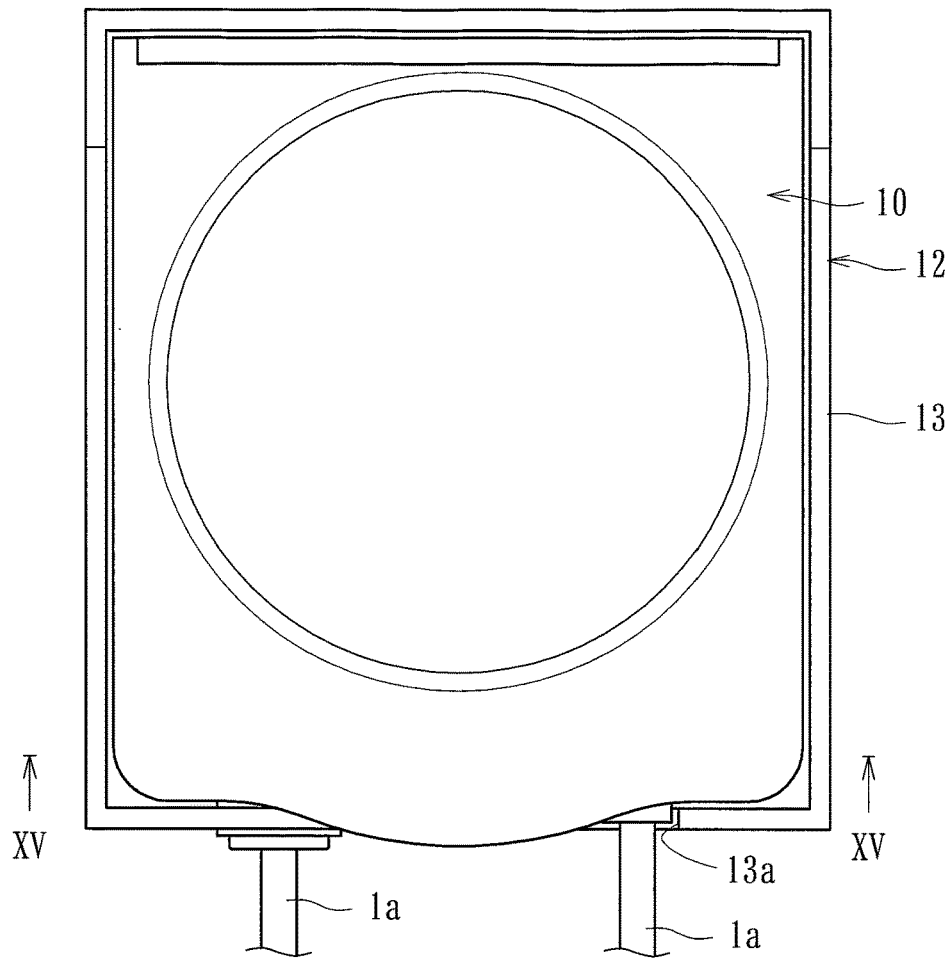
[FIG 15]
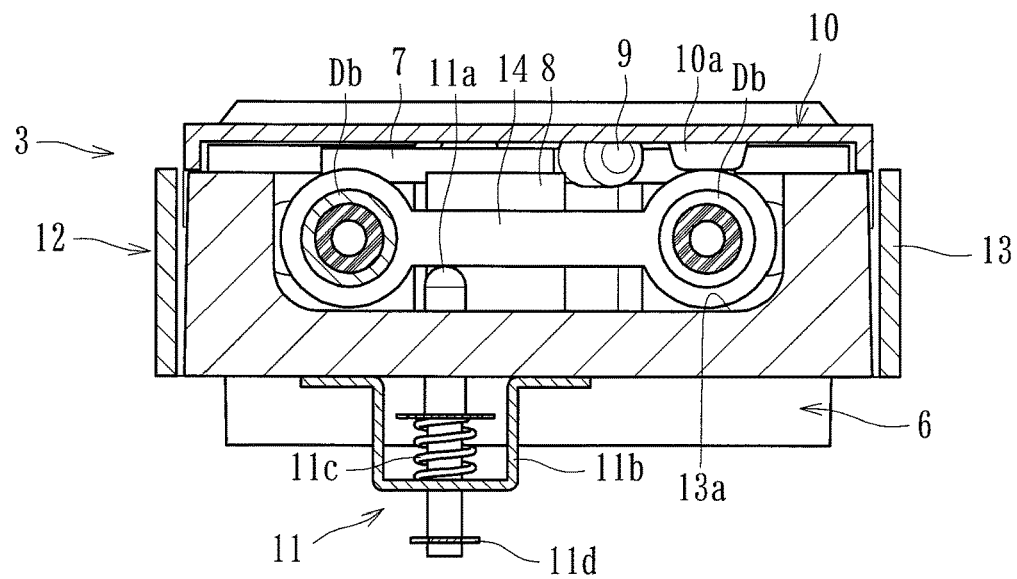

[FIG 16]
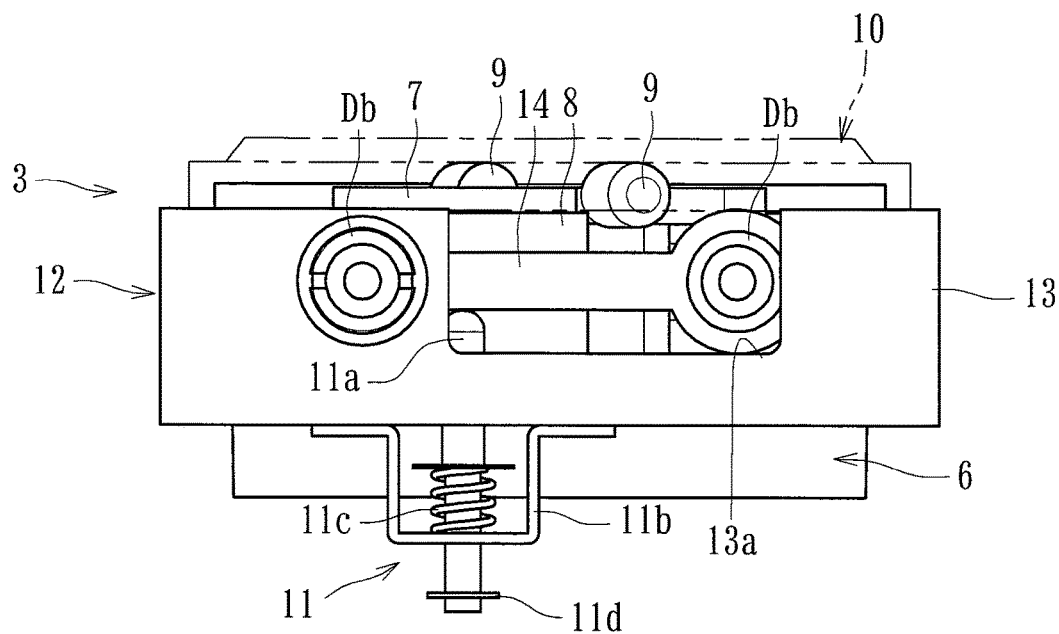
[FIG 17]
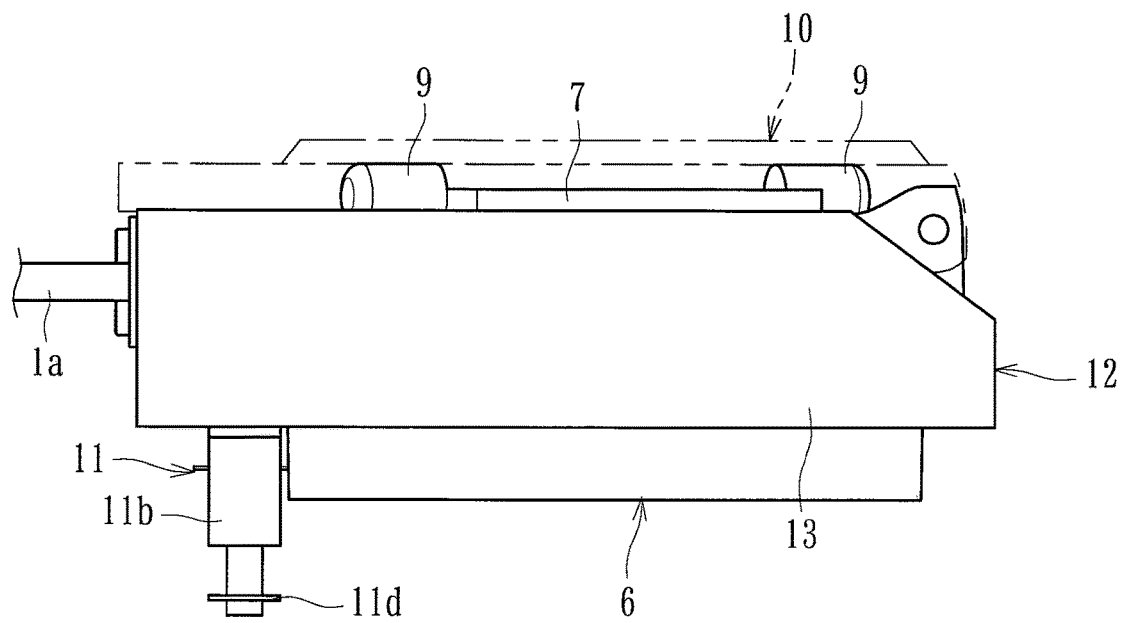

[FIG 18]
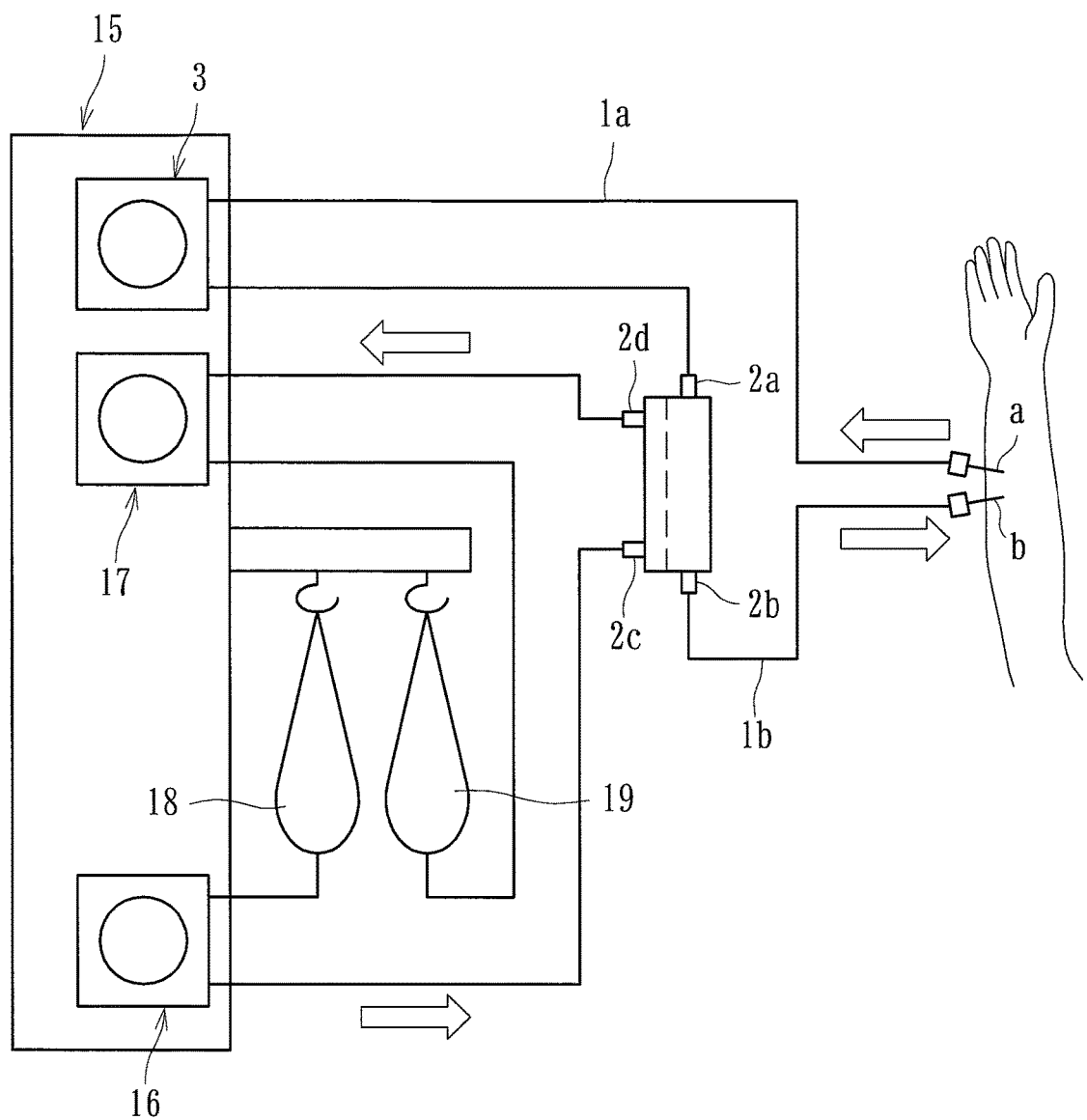

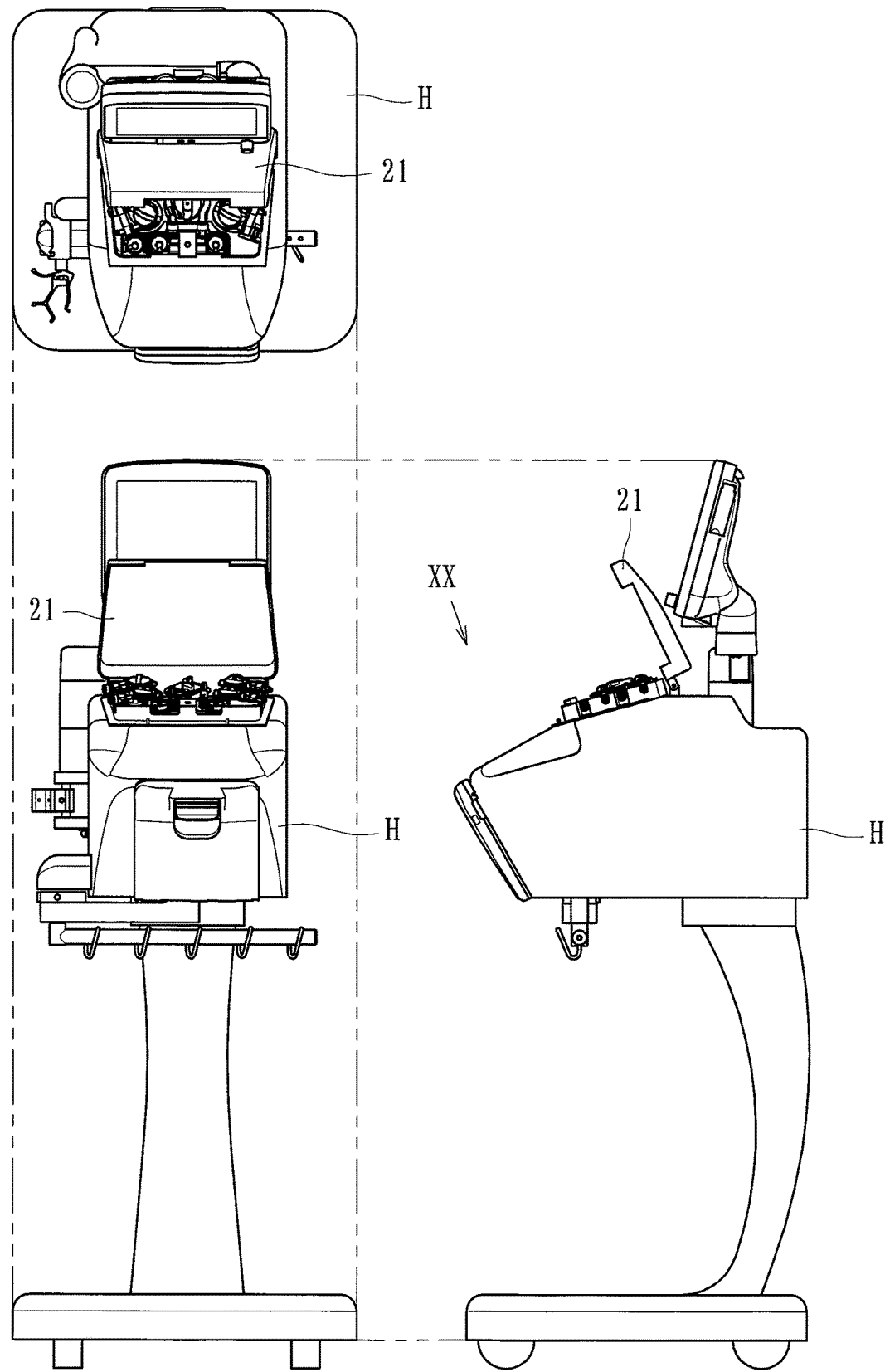
[FIG 19]

[FIG 20]
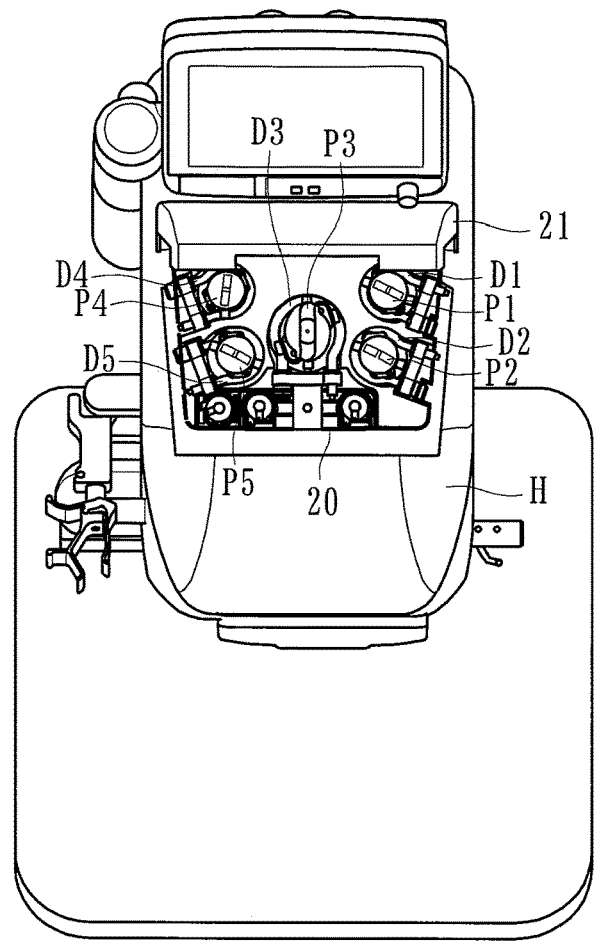
[FIG 21]
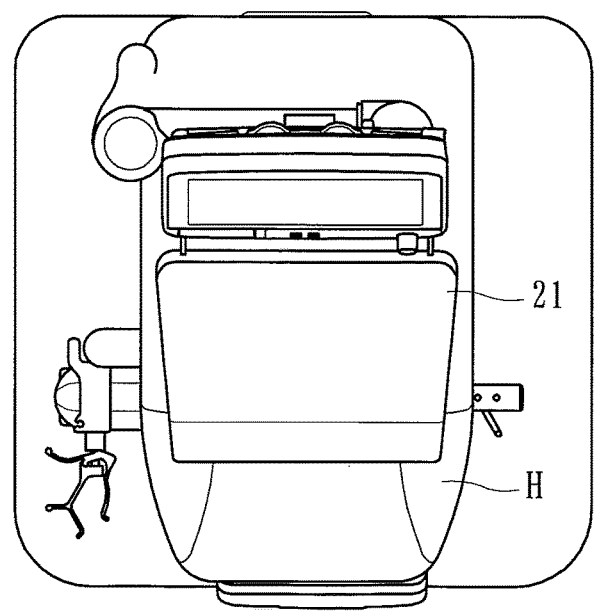

INSTALLATION MEMBER AND PERISTALTIC PUMP

FIELD

The present teachings relates to an installation member to be detachably attached to a peristaltic pump, and the peristaltic pump.

BACKGROUND

In general, in dialysis treatment, a blood circuit composed of a flexible tube is used to extracorporeally circulate the blood of a patient. The blood circuit mainly includes an arterial blood circuit having a leading end attached to an arterial puncture needle for collecting the blood of a patient, and a venous blood circuit having a leading end attached to a venous puncture needle for returning the blood to the patient. A dialyzer is disposed between the arterial blood circuit and the venous blood circuit, and the blood which is extracorporeally circulated is purified.

Part of the arterial blood circuit is connected to a flexible tube to be peristaltic which has more flexibility and a larger diameter than the rest, and the part is configured to be attached to a peristaltic pump disposed in the dialysis device. Normally, the peristaltic blood pump mainly includes a stator having an attachment recessed portion in which a flexible tube to be peristaltic is attachable; a retaining means that can firmly retain the flexible tube to be peristaltic attached to the attachment recessed portion; a rotor that is rotatably driven in the attachment recessed portion; and a roller that is formed in the rotor and that imparts peristaltic motion to the flexible tube to be peristaltic while compressing the flexible tube to be peristaltic.

In order to attach a flexible tube to be peristaltic to a peristaltic blood pump, a worker such as a medical professional needs to take and rotate the flexible tube to be peristaltic along the inner circumferential wall surface of the attachment recessed portion while manually rotating the rotor little by little. In other words, only a small clearance is provided between the inner circumferential wall surface of the attachment recessed portion and the roller due to the necessity of compressing and imparting peristaltic motion to the flexible tube at the time of rotational drive of the rotor, and thus in order to insert the flexible tube in the clearance, the rotor is manually rotated little by little and the flexible tube is attached to the entire attachment recessed portion. It is to be noted that attachment of such a flexible tube to be peristaltic is substantially common among not only a blood pump but all pumps called a peristaltic pump.

In the above-described peristaltic pump, work of attaching the flexible tube to be peristaltic to the attachment recessed portion of the stator is troublesome. For this reason, the applicant has proposed a peristaltic pump that allows a flexible tube to be peristaltic to be attached more easily and smoothly (see, for instance, PTL 1). The peristaltic pump is configured to regulate the movement of the flexible tube to be peristaltic in a longitudinal direction by fixing the upstream-side of the flexible tube, to be attached to the attachment recessed portion, and to allow the movement of the flexible tube to be peristaltic in a longitudinal direction in the downstream-side by the rotational driving force of the rotor, and it was expected that workability of attachment of the flexible tube to be peristaltic in the attachment recessed portion can be improved.

CITATION LIST

PTL 1: Japanese Unexamined Patent Application Publication No. 2008-2388

SUMMARY

However, since the above-described conventional peristaltic pump includes a retaining means for retaining each of the upstream-side and the downstream-side of the flexible tube to be peristaltic, work of retaining and fixing the flexible tube to be peristaltic to the retaining means needs to be performed manually, and thus there is a problem in that workability of attachment cannot be sufficiently improved. In addition, when the flexible tube to be peristaltic is detached from the stator, work of releasing the retention on each of the upstream-side and the downstream-side is needed, and thus there is a problem in that the workability at the time of detachment work is not sufficient.

The present invention has been made in view of such a situation, and provides an installation member and a peristaltic pump that allow work of attachment and work of detachment of a flexible tube to be peristaltic to and from a stator to be performed more easily and smoothly.

The present teachings provide an installation member that is to be detachably attached to a peristaltic pump including: a stator including an attachment recessed portion, in which a flexible tube to be peristaltic which allows a fluid such as blood to flow, is attached; a rotor that is rotatably driven in the attachment recessed portion; and a roller that is formed in the rotor and that causes the fluid to flow in the flexible tube to be peristaltic by imparting peristaltic motion to the flexible tube to be peristaltic attached to the attachment recessed portion in a longitudinal direction in association with rotation of the rotor while compressing the flexible tube to be peristaltic in a radial direction, characterized in that the installation member includes: a main body that is attachable to a predetermined portion of the stator, and that is formed integrally with one of an upstream-side fixing portion and a downstream-side fixing portion of the flexible tube to be peristaltic; and a notch portion that is formed in the main body, and that allows the other one of the upstream-side fixing portion and the downstream-side fixing portion of the flexible tube to be peristaltic to be positioned.

The present teachings provide the installation member according to the teachings herein in that the installation member further comprises a connection portion that connects a vicinity of the upstream-side fixing portion and a vicinity of the downstream-side fixing portion of the flexible tube to be peristaltic.

The present teachings provide the installation member according to the teachings herein in that the main body is comprised of a frame-shaped member formed by copying a shape of an outer circumferential surface of the stator, and is attachable to the outer circumferential surface of the stator.

The teachings herein provide the installation member according to the teachings herein in that the main body and the flexible tube to be peristaltic are comprised of disposable parts.

The present teachings provide the installation member according to the teachings herein in that a plurality of pieces of the flexible tube to be peristaltic is formed integrally with the main body, and the installation member is detachably attached to each of a plurality of pieces of the peristaltic pump.

The present teachings provide a peristaltic pump characterized in that the peristaltic pump comprises a stator to which the main body according to the teachings herein is detachably attached.

The present teachings provide the peristaltic pump according to the teachings herein in that a guide pin projecting to a side of an inner circumferential wall surface of an attachment recessed portion is formed in the rotor, the main body is attached to the predetermined portion of the stator, and the rotor is rotationally driven in a state where the other one of the upstream-side fixing portion and the downstream-side fixing portion of the flexible tube to be peristaltic is positioned at the notch portion, thereby allowing the flexible tube to be peristaltic to be moved to an attachment position.

The present teachings provide the peristaltic pump according to the teachings herein in that the peristaltic pump further comprises a cover that is attached to the stator in a freely openable and closable manner, and that coves the attachment recessed portion in a closed state; and a press projection portion that is formed in the cover, and that allows the other one of the upstream-side fixing portion and the downstream-side fixing portion of the flexible tube to be peristaltic to be pressed to the notch portion in a state where the cover is closed.

The present teachings provide the peristaltic pump according to the teachings herein in that the peristaltic pump further comprises a press means that is able to press the flexible tube to be peristaltic in a direction in which the flexible tube is detached from the attachment recessed portion.

According to the teachings herein, the installation member includes: a main body that is attachable to a predetermined portion of the stator, and that is formed integrally with one of an upstream-side fixing portion and a downstream-side fixing portion of the flexible tube to be peristaltic; and a notch portion that is formed in the main body, and that allows the other one of the upstream-side fixing portion and the downstream-side fixing portion of the flexible tube to be peristaltic to be positioned. Thus, work of attachment and work of detachment of the flexible tube to be peristaltic to and from the stator can be done more easily and smoothly.

According to the teachings herein, the installation member includes a connection portion that connects a vicinity of the upstream-side fixing portion and a vicinity of the downstream-side fixing portion of the flexible tube to be peristaltic. Thus, the flexible tube to be peristaltic can be a state of being bent in an arc shape, and the flexible tube to be peristaltic can be disposed along the attachment recessed portion in a state where the main body is attached to the stator 6.

According to the teachings herein, the main body is comprised of a frame-shaped member formed by copying a shape of an outer circumferential surface of the stator, and is attachable to the outer circumferential surface of the stator. Thus, work of attachment and work of detachment of the installation member to and from the peristaltic pump can be done more easily and reliably.

According to the teachings herein, the main body and the flexible tube to be peristaltic are comprised of disposable parts. Thus, after medical treatment is finished, the main body and the flexible tube to be peristaltic can be discarded collectively.

According to the teachings herein, a plurality of pieces of the flexible tube to be peristaltic is formed integrally with the main body, and the installation member is detachably attached to each of a plurality of pieces of the peristaltic pump. Thus, the flexible tubes to be peristaltic can be attached or detached to or from the plurality of peristaltic pumps collectively, and workability at the time of attachment and detachment can be improved.

According to the teachings herein, the peristaltic pump includes a stator to which the main body is detachably attached. Thus, a means for fixing the flexible tube to be peristaltic is unnecessary, and work of attachment and work of detachment of the flexible tube to be peristaltic to and from the stator can be done more easily and smoothly.

According to the teachings herein, a guide pin projecting to a side of an inner circumferential wall surface of an attachment recessed portion is formed in the rotor, the main body is attached to the predetermined portion of the stator, and the rotor is rotationally driven in a state where the other one of the upstream-side fixing portion and the downstream-side fixing portion of the flexible tube to be peristaltic is positioned at the notch portion, thereby allowing the flexible tube to be peristaltic to be moved to an attachment position. Thus, attachment of the flexible tube to be peristaltic to the attachment recessed portion can be done more easily.

According to the teachings herein, the peristaltic pump further comprises: a cover that is attached to the stator in a freely openable and closable manner, and that coves the attachment recessed portion in a closed state; and a press projection portion that is formed in the cover, and that allows the other one of the upstream-side fixing portion and the downstream-side fixing portion of the flexible tube to be peristaltic to be pressed to the notch portion in a state where the cover is closed. Thus, by closing the cover, the other one of the upstream-side fixing portion and the downstream-side fixing portion of the flexible tube to be peristaltic can be reliably and smoothly positioned at the notch portion.

According to the teachings herein, the peristaltic pump further comprises a press means that is able to press the flexible tube to be peristaltic in a direction in which the flexible tube is detached from the attachment recessed portion. Thus, work of detachment of the flexible tube to be peristaltic from the stator can be done more easily and smoothly.

BRIEF DESCRIPTION OF DRAWINGS

FIG. 1 is a schematic illustration depicting a blood purification apparatus that uses a peristaltic pump according to an embodiment of the present invention.

FIG. 2 is a schematic illustration depicting a flexible tube to be peristaltic applied to the peristaltic pump.

FIG. 3 is a perspective view illustrating the peristaltic pump.

FIG. 4 is a plan view illustrating the peristaltic pump.

FIG. 5 is a front view illustrating the peristaltic pump.

FIG. 6 is a side view illustrating the peristaltic pump.

FIG. 7 is a perspective view illustrating an installation member according to an embodiment of the present invention.

FIG. 8 is a three-view illustrating the installation member.

FIG. 9 is a perspective view illustrating a state (a cover is in an opened state) where the installation member is installed in the peristaltic pump.

FIG. 10 is a plan view illustrating a state (the cover is in an opened state) where the installation member is installed in the peristaltic pump.

FIG. 11 is a front view illustrating a state (the cover is in an opened state) where the installation member is installed in the peristaltic pump.

FIG. 12 is a side view illustrating a state (the cover is in an opened state) where the installation member is installed in the peristaltic pump.

FIG. 13 is a perspective view illustrating a state (the cover is in a closed state) where the installation member is installed in the peristaltic pump.

FIG. 14 is a plan view illustrating a state (the cover is in a closed state) where the installation member is installed in the peristaltic pump.

FIG. 15 is a sectional view taken along line XV-XV in FIG. 14.

FIG. 16 is a front view illustrating a state (the cover is in a closed state) where the installation member is installed in the peristaltic pump.

FIG. 17 is a side view illustrating a state (the cover is in a closed state) where the installation member is installed in the peristaltic pump.

FIG. 18 is a schematic illustration depicting a blood purification apparatus that uses a peristaltic pump according to another embodiment of the present invention.

FIG. 19 is a three-view illustrating a blood purification apparatus that uses a peristaltic pump according to still another embodiment of the present invention.

FIG. 20 is a plan view (view as seen from arrow XX in FIG. 19) illustrating the blood purification apparatus (the cover is an opened state).

FIG. 21 is a plan view illustrating the blood purification apparatus (the cover is a closed state).

DETAILED DESCRIPTION

Hereinafter, an embodiment of the present invention will be described with reference to the drawings. A peristaltic pump according to the present embodiment is applied to a peristaltic blood pump that flows blood in a blood circuit by imparting peristaltic motion to a flexible tube to be peristaltic, which constitutes part of the blood circuit for extracorporeally circulating blood while compressing the flexible tube in a radial direction. Hereinafter, a hemodialysis apparatus (including a blood circuit) that uses the peristaltic blood pump will be described.

As illustrated in FIG. 1, the hemodialysis apparatus mainly includes a blood circuit 1 to which a dialyzer 2 is connected, and a dialysis device 5 that ultrafilters blood while supplying dialysate to the dialyzer 2. As illustrated in FIG. 1, the blood circuit 1 mainly includes an arterial blood circuit 1a and a venous blood circuit 1b each formed of a flexible tube, and the dialyzer 2 is connected in between the arterial blood circuit 1a and the venous blood circuit 1b.

The dialyzer 2 is formed by housing in a case unit a plurality of hollow fibers in which fine holes (bores) are formed, and in the case unit, a blood inlet port 2a, a blood outlet port 2b, a dialysate inlet port 2c, and a dialysate outlet port 2d are formed, between which the blood inlet port 2a is connected to the base end of the arterial blood circuit 1a, and the blood outlet port 2b is connected to the base end of the venous blood circuit 1b. In addition, the dialysate inlet port 2c and the dialysate outlet port 2d are respectively connected to a dialysate inlet line L1 and a dialysate outlet line L2 that are installed extending from the dialysis device 5.

The leading end of the arterial blood circuit 1a is connected to an arterial puncture needle a, and a peristaltic pump 3 is disposed as a blood pump at some midpoint in the arterial blood circuit 1a, whereas the leading end of the venous blood circuit 1b is connected to a venous puncture needle b, and an air trap chamber 4 for removing bubbles is disposed at some midpoint in the venous blood circuit 1b.

When the peristaltic pump 3 is driven with the arterial puncture needle a and the venous puncture needle b inserted in a patient, the blood of the patient reaches the dialyzer 2 through the arterial blood circuit 1a, and is purified by the dialyzer 2, then returns to the body of the patient through the venous blood circuit 1b while bubbles are removed by the air trap chamber 4. That is, the blood of the patient is purified by the dialyzer 2 while being extracorporeally circulated through the blood circuit 1.

On the other hand, part of the arterial blood circuit 1a is connected to a flexible tube D to be peristaltic which has more flexibility and a larger diameter than the rest as illustrated in FIG. 2, and the part (the flexible tube D to be peristaltic) is configured to be attached to the peristaltic pump 3 disposed in the dialysis device 5. As illustrated in FIGS. 3 to 6, the peristaltic pump 3 mainly includes a stator 6, a rotor 7 that is rotatably driven in the stator 6, a roller 8 formed in the rotor 7, a pair of upper and lower guide pins 9, a cover 10, and a press means 11.

The later-described main body 13 of the installation member 12 is detachably attached to the stator 6, in which an attachment recessed portion 6a is formed in which the flexible tube D to be peristaltic is attached, and the stator 6 is configured so that the flexible tube D to be peristaltic is attached along an inner circumferential wall surface 6aa that forms the attachment recessed portion 6a. In addition, in the stator 6, an attachment portion 6b is formed in a portion where a connection portion 14 is positioned when the later-described installation member 12 is attached to the stator 6. Furthermore, the rotor 7, which is rotatably driven by a motor (not illustrated), is disposed in approximately the center of the attachment recessed portion 6a. A pair of rollers 8 and the guide pins 9 are disposed in the lateral surface (the surface facing the inner circumferential wall surface aa) of the rotor 7.

The roller 8 is rotatable around a rotational shaft formed on the outer peripheral side of the rotor 7, and allows blood to flow in the blood circuit 1 by imparting peristaltic motion to the flexible tube D to be peristaltic attached to the attachment recessed portion 6a in a longitudinal direction (flow direction of the blood) in association with rotation of the rotor 7 while compressing the flexible tube D in a radial direction. That is, when the flexible tube D to be peristaltic is attached to the attachment recessed portion 6a and the rotor 7 is rotationally driven, the flexible tube D to be peristaltic is compressed between the roller 8 and the inner circumferential wall surface 6aa, and peristaltic motion can be imparted to the flexible tube D in a rotation direction (longitudinal direction) in association with rotational drive of the rotor 7. Such peristaltic action causes the blood in the blood circuit 1 to flow in the rotation direction of the rotor 7, thereby making it possible to circulate the blood extracorporeally through the blood circuit 1.

The guide pins 9 are formed of a pin-shaped member that projects from the upper end side and the lower end side of the rotor 7 toward the inner circumferential wall surface 6aa, and the flexible tube D to be peristaltic is held between those pins. That is, it is designed that when the rotor 7 is driven, the flexible tube D to be peristaltic is held at a regular position (attachment position) by the upper and lower guide pins 9, and the flexible tube D to be peristaltic is not separated from the attachment recessed portion 6a by the upper-side guide pin 9.

The cover 10 is attached to the stator 6 in a freely openable and closable manner, and coves the attachment recessed portion 6a in a closed state as illustrated in FIGS. 13 and 14, and can prevent entry of foreign matters into the attachment recessed portion 6*a* at the time of rotational drive of the rotor 7. Also, in a state where the later-described installation member 12 is not attached to the peristaltic pump 3, even in a closed state of the cover 10, the attachment recessed portion 6*a* faces the outside (front side) via the attachment portion 6*b*.

Here, the present embodiment is configured so that the installation member 12 is installed in the above-mentioned peristaltic pump 3. As illustrated in FIGS. 7 and 8, such installation member 12 is mountable in a predetermined portion of the stator 6, and includes: a main body 13 that is formed integrally with one (the downstream-side fixing portion Db in the present embodiment) of the upstream-side fixing portion Da and the downstream-side fixing portion Db of the flexible tube D to be peristaltic; a notch portion 13*a* that is formed in the main body 13, and that allows the other one (the upstream-side fixing portion Da in the present embodiment) of the upstream-side fixing portion Da and the downstream-side fixing portion Db of the flexible tube D to be peristaltic to be positioned at the notch portion 13*a*; and a plate like connection portion 14 that connects the vicinity of the upstream-side fixing portion Da and the vicinity of the downstream-side fixing portion Db of the flexible tube D to be peristaltic.

That is, the flexible tube D to be peristaltic having both ends each connected to the blood circuit 1 (arterial blood circuit 1*a*), the downstream-side fixing portion Db thereof is integrally fixed to the installation member 12, and the flexible tube D to be peristaltic is bent in an arc shape (ring shape) by the connection portion 14 and is held in the main body 13. Like this, the installation member 12, in which the flexible tube D to be peristaltic is formed, is comprised of disposable parts (disposable articles), and after blood purification treatment is finished, the installation member 12 is discarded along with the blood circuit 1.

The main body 13 according to the present embodiment is comprised of a frame-shaped member (a cylindrical member with a rectangular outside shape) which is formed by copying the outer circumferential surface shape of the stator 6, and as illustrated in FIGS. 9 to 12, can be fitted and attached on the outer circumferential surface (predetermined portion) of the stator 6. When the main body 13 is fitted and attached to the stator 6, the upstream-side fixing portion Da and the downstream-side fixing portion Db of the flexible tube D to be peristaltic, and the connection portion 14 are positioned on the attachment portion 6*b*. It is to be noted that when the main body 13 is attached to the stator 6, a predetermined portion of the flexible tube D to be peristaltic is positioned on the guide pin 9, and thus the upstream-side fixing portion Da of the flexible tube D to be peristaltic is in a state (a state of being spaced above by a predetermined dimension) of floating above from the notch portion 13*a*.

On the other hand, in the cover 10 included in the peristaltic pump 3, a press projection portion 10*a* is formed that can press the other one (the upstream-side fixing portion Da in the present embodiment) of the upstream-side fixing portion Da and the downstream-side fixing portion Db of the flexible tube D to be peristaltic up to the notch portion 13*a* of the main body 13 in a closed state of the cover 10. That is, the press projection portion 10*a* in a projection shape is integrally formed in the back surface (the surface facing the stator 6 in a closed state) of the cover 10, and in a process in which the cover 10 is closed, the press projection portion 10*a* interferes with and presses the other one (the upstream-side fixing portion Da) of the upstream-side fixing portion Da and the downstream-side fixing portion Db of the flexible tube D to be peristaltic in the direction to the other one, and as illustrated in FIGS. 13 to 17, the press projection portion 10*a* causes the other one (the upstream-side fixing portion Da in the present embodiment) of the upstream-side fixing portion Da and the downstream-side fixing portion Db of the flexible tube D to be peristaltic to be moved and positioned at the notch portion 13*a*.

Thus, the main body 13 is fitted and attached on the outer circumferential surface (predetermined portion) of the stator 6, and the rotor 7 is rotationally driven in a state where the other one (the upstream-side fixing portion Da) of the upstream-side fixing portion Da and the downstream-side fixing portion Db of the flexible tube D to be peristaltic is positioned at the notch portion 13*a*, thereby making it possible to move the flexible tube D to be peristaltic to the attachment position (the position between the upper and lower guide pins 9).

That is, in state where the main body 13 is fitted and attached on the outer circumferential surface (predetermined portion) of the stator 6, and the other one (the upstream-side fixing portion Da) of the upstream-side fixing portion Da and the downstream-side fixing portion Db of the flexible tube D to be peristaltic is positioned at the notch portion 13*a*, the attachment height of the upstream-side fixing portion Da and the downstream-side fixing portion Db of the flexible tube D to be peristaltic is located between the upper and lower guide pins 9. When the rotor 7 is rotationally driven in the state, the flexible tube D to be peristaltic is passed over the upper guide pin 9 and can be moved to the attachment position.

Furthermore, the peristaltic pump 3 according to the present embodiment includes a press means 11 that can press the flexible tube D to be peristaltic in a direction in which the flexible tube D is detached from the attachment recessed portion 6*a*. The press means 11 is attached to the stator 6 of the peristaltic pump 3, and includes a pushrod 11*a* that is disposed in the attachment portion 6*b* of the stator 6 in a projecting manner, a housing 11*b* that houses the base end side of the pushrod 11*a*, a spring 11*c* that is disposed in the housing 11*b* and urges the pushrod 11*a* in a projection direction (upward in FIG. 5), and a retaining ring 11*d* that is attached to the base end of the pushrod 11*a* for preventing coming off from the housing 11*b*.

Thus, when the main body 13 of the installation member 12 is fitted and attached on the outer circumferential surface of the peristaltic pump 3, as illustrated in FIG. 11, it is designed that the leading end of pushrod 11*a* comes into contact with the connection portion 14. When the cover 10 is closed in this state, the other one (the upstream-side fixing portion Da side) side of the upstream-side fixing portion Da and the downstream-side fixing portion Db of the flexible tube D to be peristaltic is pressed by the press projection portion 10*a*, and thus the pushrod 11*a* is pressed by the connection portion 14, and is moved toward the housing 11*b* side (downward in FIGS. 15, 16) against the urging force of the spring 11*c* as illustrated in FIGS. 15 and 16.

For instance, when medical treatment is completed and the cover 10 is opened, the pressing force from the press projection portion 10*a* is released, and thus the connection portion 14 is pressed by the urging force of the spring 11*c* of the pushrod 11*a*, and the flexible tube D to be peristaltic is moved in a direction in which the flexible tube D is detached from the attachment recessed portion 6*a* (upward in FIG. 15). In this manner, in the present embodiment, the flexible tube D to be peristaltic is attachable to the attachment recessed portion 6*a* by closing the cover 10 and rotationally driving the rotor 7, and the flexible tube D to be peristaltic can be detached from the attachment recessed portion 6a by opening the cover 10.

Next, a method of attaching the flexible tube D to be peristaltic to the peristaltic pump 3 according to the present embodiment will be described.

First, the cover 10 is made to be in an opened state, and the main body 13 is fitted and attached on the outer circumferential surface, and thus the installation member 12 is installed in the peristaltic pump 3. Thus, as illustrated in FIGS. 9 to 12, the flexible tube D to be peristaltic bent in an arc shape is positioned along the inner circumferential wall surface 6aa of the attachment recessed portion 6a of the stator 6, and the upstream-side fixing portion Da and the downstream-side fixing portion Db are positioned in the attachment portion 6b of the stator (however, the upstream-side fixing portion Da is in a state of floating above from the attachment portion 6b). It is to be noted that the connection portion 14 connecting the vicinity of the upstream-side fixing portion Da and the vicinity of the downstream-side fixing portion Db is in contact with the leading end of the pushrod 11a.

Then, closing the cover 10 causes the press projection portion 10a to press the upstream-side fixing portion Da, and the connection portion 14 is swung around the downstream-side fixing portion Db as the center, then as illustrated in FIGS. 13 to 17, the upstream-side fixing portion Da reaches the notch portion 13a. At this point, the upstream-side fixing portion Da is moved to a position with approximately the same height as the height of the downstream-side fixing portion Db, and is held at the position. It is to be noted that the pushrod 11a is pressed by the connection portion 14 and is moved downward against the urging force of the spring 11c, and is held at the position.

Subsequently, when the rotor 7 is rotationally driven in a closed state of the cover 10, the flexible tube D to be peristaltic is moved between the upper and lower guide pins 9 in association with the rotational operation of the roller 8, and is set at the attachment position. In this attachment state, when the arterial puncture needle a and the venous puncture needle b are inserted in a patient, the blood of the patient is extracorporeally circulated through the blood circuit 1, and in this process, the blood is purified by the dialyzer 2.

When the cover 10 is opened after the blood purification treatment is completed and the rotational drive of the rotor 7 is stopped, the pushrod 11a is moved upward by the urging force of the spring 11c, and thus when the flexible tube D to be peristaltic is pulled above the upper guide pin 9, the state illustrated in FIGS. 9 to 12 is assumed. Thus, the installation member 12 is detached from the peristaltic pump 3, and the installation member 12 (the main body 13 with which the flexible tube D to be peristaltic is integrally formed) can be thereby discarded along with the blood circuit 1.

According to the above-described embodiment, since the installation member includes: the main body 13 that is attachable in a predetermined portion of the stator 6, and that is formed integrally with one of the upstream-side fixing portion Da and the downstream-side fixing portion Db of the flexible tube D to be peristaltic; and the notch portion 13a that is formed in the main body 13, and that allows the other one of the upstream-side fixing portion Da and the downstream-side fixing portion Db of the flexible tube D to be peristaltic to be positioned at the notch portion 13a, work of attachment and work of detachment of the flexible tube D to be peristaltic to and from the stator 6 can be done more easily and smoothly.

In addition, the installation member 12 has the connection portion 14 connecting the vicinity of the upstream-side fixing portion Da and the vicinity of the downstream-side fixing portion Db of the flexible tube D to be peristaltic, and thus the flexible tube D to be peristaltic can be a state (see FIGS. 7 and 8) of being bent in an arc shape, and the flexible tube D to be peristaltic can be disposed (see FIGS. 9 and 10) along the attachment recessed portion 6a in a state where the main body 13 of the installation member 12 is attached to the stator 6. In addition, the separation dimension between the upstream-side fixing portion Da and the downstream-side fixing portion Db of the flexible tube D to be peristaltic can be constant (predetermine dimension) by the connection portion 14, and thus when the cover 10 is closed, the other one of the upstream-side fixing portion Da and the downstream-side fixing portion Db can be reliably positioned at the notch portion 13a.

Furthermore, the main body 13 according to the present embodiment is comprised of a frame-shaped member formed by copying the shape of the outer circumferential surface of the stator 6, and is attachable to the outer circumferential surface of the stator 6. Therefore, work of attachment and work of detachment of the installation member 12 to and from the peristaltic pump 3 can be done more easily and reliably. Still furthermore, since the main body 13 and the flexible tube D to be peristaltic according to the present embodiment are comprised of disposable parts, and after medical treatment is finished, the main body 13 and the flexible tube D to be peristaltic can be discarded collectively.

Also, since the peristaltic pump 3 according to the present embodiment includes the stator 6 to which the main body 13 of the installation member 12 is detachably attached, a means (such as a retaining means for retaining and fixing each of the upstream-side fixing portion and the downstream-side fixing portion) for fixing the flexible tube D to be peristaltic is unnecessary, and work of attachment and work of detachment of the flexible tube D to be peristaltic to and from the stator 6 can be done more easily and smoothly.

Furthermore, in the rotor 7 according to the present embodiment, the guide pins 9 projecting to the side of the inner circumferential wall surface 6aa of the attachment recessed portion 6a are formed, the main body 13 is attached to a predetermined portion of the stator 6, and the rotor 7 is rotationally driven in a state where the other one of the upstream-side fixing portion Da and the downstream-side fixing portion Db of the flexible tube D to be peristaltic is positioned at the notch portion 13a, thereby allowing the flexible tube D to be peristaltic to be moved to the attachment position. Thus, attachment of the flexible tube D to be peristaltic to the attachment recessed portion 6a can be done more easily.

Also, the peristaltic pump 3 includes the cover 10 that is attached to the stator 6 in a freely openable and closable manner, and that coves the attachment recessed portion 6a in a closed state; and the press projection portion 10a that is formed in the cover 10, and that allows the other one of the upstream-side fixing portion Da and the downstream-side fixing portion Db of the flexible tube D to be peristaltic to be pressed to the notch portion 13a in a state where the cover 10 is closed. Thus, by closing the cover 10, the other one of the upstream-side fixing portion Da and the downstream-side fixing portion Db of the flexible tube D to be peristaltic can be reliably and smoothly positioned at the notch portion 13a.

Still furthermore, the peristaltic pump 3 includes the press means 11 that is able to press the flexible tube D to be peristaltic in a direction in which the flexible tube D is detached from the attachment recessed portion 6a. Thus, work of detachment of the flexible tube D to be peristaltic from the stator 6 can be done more easily and smoothly. It is to be noted that the press means 11 according to the present embodiment presses the flexible tube D to be peristaltic by moving the pushrod 11a using the urging force of the spring 11c. However, for instance, the flexible tube D to be peristaltic may be pressed by moving a separate actuator such as a cylinder or a motor.

On the other hand, in the installation member 12 according to the above-described embodiment, single flexible tube D to be peristaltic is integrally formed in the main body 13. However, instead of this, a plurality of the flexible tubes D to be peristaltic may be integrally formed in the main body 13, and each is detachably attached to a corresponding one of a plurality of peristaltic pumps (not necessarily blood pumps). In this case, the flexible tubes to be peristaltic can be attached or detached to or from the plurality of peristaltic pumps collectively, and workability at the time of attachment and detachment can be improved.

For instance, as illustrated in FIG. 18, when the invention is applied to a blood purification apparatus which includes a storage bag 18 that stores dialysate to be supplied to the dialyzer 2, and a storage bag 19 that stores drainage discharged from the dialyzer 2, and in which in addition to the peristaltic pump 3 as a blood pump, a peristaltic pump 16 for conveying the dialysate of the storage bag 18 to the dialyzer 2, and a peristaltic pump 17 for conveying the drainage from the dialyzer 2 to the storage bag 19 are formed in a dialysis device 15, main bodies may be provided which are installed in the peristaltic pump 3 as a blood pump and the peristaltic pumps 16, 17, and respective flexible tubes D to be peristaltic corresponding to the peristaltic pumps (3, 16, 17) may be integrally formed in the main bodies.

Furthermore, as illustrated in FIGS. 19 to 21, when the invention is applied to a dialysis apparatus H including: a plurality of peristaltic pumps (P1 to P5), the installation member may include a main body 20 that can surround the plurality of peristaltic pumps (P1 to P5); and flexible tubes (D1 to D5) to be peristaltic corresponding to the peristaltic pumps (P1 to P5), where the flexible tubes (D1 to D5) to be peristaltic are integrally formed in the main body 20 and each of the flexible tubes (D1 to D5) has a notch portion.

Also, it is preferable that a cover 21 be provided that covers the space above the peristaltic pumps (P1 to P5) in the dialysis apparatus H, and a press projection portion corresponding to the press projection portion 10a of the above-described embodiment be formed in the cover 21. Thus, by closing the cover 21 after the main body 20 is installed, the flexible tubes (D1 to D5) to be peristaltic can be attached to the peristaltic pumps (P1 to P5) collectively.

Although the present embodiment has been described, the present invention is not limited to this, and for instance, the installation member may include: a main body that is formed integrally with the upstream-side fixing portion of the flexible tube to be peristaltic; and a notch portion that is formed in the main body, and that allows the downstream-side fixing portion of the flexible tube to be peristaltic to be positioned at the notch portion. Also, instead of the installation member 12, an installation member may include a component not connected by the connection portion 14 or a main body in a shape other than a frame-shaped member. Furthermore, in addition to a blood pump and a substitution pump, the peristaltic pump may be one of various other types.

The peristaltic pump may have other functions as long as the peristaltic pump includes: a main body that is attachable to a predetermined portion of the stator, and that is formed integrally with one of an upstream-side fixing portion and a downstream-side fixing portion of the flexible tube to be peristaltic; a notch portion that is formed in the main body, and that allows the other one of the upstream-side fixing portion and the downstream-side fixing portion of the flexible tube to be peristaltic to be positioned at the notch portion; and a stator to which the main body is detachably attached.

REFERENCE SIGNS LIST

1 Blood circuit
1a Arterial blood circuit
1b Venous blood circuit
2 Dialyzer
3 Peristaltic pump
4 Air trap chamber
5 Dialysis device
6 Stator
7 Rotor
8 Roller
9 Guide pin
10 Cover
10a Press projection portion
11 Press means
12 Attachment member
13 Main body
13a Notch portion
14 Connection portion
15 Dialysis device
16, 17 Peristaltic pump
18, 19 Storage bag
20 Main body
21 Cover

I claim:
1. An installation member that is configured to be detachably attached to a peristaltic pump that includes:
   a stator including an attachment recessed portion, in which a flexible tube to be peristaltic which allows a fluid to flow, is attached;
   a rotor that is rotatably driven in the attachment recessed portion; and
   a roller that is formed in the rotor and that causes the fluid to flow in the flexible tube to be peristaltic by imparting peristaltic motion to the flexible tube to be peristaltic attached to the attachment recessed portion in a longitudinal direction in association with rotation of the rotor while compressing the flexible tube to be peristaltic in a radial direction,
   wherein the installation member comprises:
   a main body that is removably attachable to a predetermined portion of the stator by inserting the peristaltic pump within confines of the main body so that the flexible tube is positioned between the rotor and the stator in the attachment recessed portion,
   an upstream-side fixing portion and a downstream-side fixing portion of the flexible tube to be peristaltic, where one of the upstream-side fixing portion and a downstream-side fixing portion is integrally formed with and fixed to the main body forming a pivot portion of the flexible tube to be peristaltic; and
   a notch portion that is formed in the main body, with an other one of the upstream-side fixing portion and the downstream-side fixing portion of the flexible tube positioned at the notch portion forming a movable portion of the flexible tube, and the notch portion allowing the movable portion of the flexible tube to be inserted into the attachment recessed portion of the stator;

wherein the flexible tube is inserted into the attachment recessed portion of the stator by rotating the flexible tube to be peristaltic about the pivot portion so that the movable portion is movable above the peristaltic pump as the peristaltic pump is inserted within the confines of the main body; and wherein the installation member is disposable and configured to be discarded after use.

2. The installation member according to claim 1, further comprising:
a connection portion free of contact with the main body that connects a vicinity of the upstream-side fixing portion and a vicinity of the downstream-side fixing portion of the flexible tube to be peristaltic.

3. The installation member according to claim 2, wherein the main body is comprised of a frame-shaped member formed by copying a shape of an outer circumferential surface of the stator, and is attachable to the outer circumferential surface of the stator.

4. The installation member according to claim 3, wherein the main body and the flexible tube to be peristaltic are comprised of disposable parts.

5. The installation member according to claim 4, wherein a plurality of pieces of the flexible tube to be peristaltic is formed integrally with the main body, and the installation member is detachably attached to each of a plurality of pieces of the peristaltic pump.

6. The installation member according to claim 5, comprising the stator being detachable attached to the main body.

7. The installation member according to claim 2, wherein a plurality of pieces of the flexible tube to be peristaltic is formed integrally with the main body, and the installation member is detachably attached to each of a plurality of pieces of the peristaltic pump.

8. The installation member according to claim 2, comprising the stator being detachably attached to the main body.

9. The installation member according to claim 1, wherein the main body is comprised of a frame-shaped member formed by copying a shape of an outer circumferential surface of the stator, the outer circumferential surface being formed by one or more interconnecting faces; and wherein the main body is attachable to the outer circumferential surface of the stator so that the main body abuts each of the one or more interconnecting faces.

10. The installation member according to claim 1, wherein a plurality of pieces of the flexible tube to be peristaltic is formed integrally with the main body, and the installation member is detachably attached to each of a plurality of pieces of the peristaltic pump.

11. The installation member according to claim 1, comprising the stator being detachably attached to the main body.

12. The peristaltic pump according to claim 11, wherein a guide pin projecting to a side of an inner circumferential wall surface of the attachment recessed portion is formed in the rotor, the main body is attached to the predetermined portion of the stator, and the rotor is rotationally driven when the flexible tube to be peristaltic is in the attachment recessed portion.

13. The peristaltic pump according to claim 12, further comprising:
a cover that is attached to the stator in a freely openable and closable manner, and that covers the attachment recessed portion in a closed state; and
a press projection portion that is formed in the cover, and that allows the other one of the upstream-side fixing portion and the downstream-side fixing portion of the flexible tube to be peristaltic to be pressed to the notch portion in a state where the cover is closed.

14. The peristaltic pump according to claim 13, further comprising
a press means that is able to press the flexible tube to be peristaltic in a direction in which the flexible tube to be peristaltic is detached from the attachment recessed portion by the movable portion of the flexible tube to be peristaltic being rotated about the pivot portion.

15. The peristaltic pump according to claim 12, further comprising
a press means that is able to press the flexible tube to be peristaltic in a direction in which the flexible tube to be peristaltic is detached from the attachment recessed portion by the movable portion of the flexible tube to be peristaltic being rotated about the pivot portion.

16. The peristaltic pump according to claim 11, further comprising:
a cover that is attached to the stator in a freely openable and closable manner, and that covers the attachment recessed portion in a closed state; and
a press projection portion that is formed in the cover, and that allows the other one of the upstream-side fixing portion and the downstream-side fixing portion of the flexible tube to be peristaltic to be pressed to the notch portion in a state where the cover is closed.

17. The peristaltic pump according to claim 11, further comprising
a press means that is able to press the flexible tube to be peristaltic in a direction in which the flexible tube to be peristaltic is detached from the attachment recessed portion by the movable portion of the flexible tube to be peristaltic being rotated about the pivot portion.

18. The peristaltic pump of claim 17, wherein a connection portion connects a vicinity of the upstream-side fixing portion and the downstream-side fixing portion of the flexible tube to be peristaltic together and the press means contacts and moves the connection portion in the direction in which the flexible tube to be peristaltic is detached from the attachment recessed portion.

19. The peristaltic pump of claim 17, wherein the press means includes a spring that biases a push rod of the press means away from the attachment position.

20. The peristaltic pump of claim 1, wherein the installation member includes:
a connection portion connecting a vicinity of the upstream-side fixing portion and the downstream-side fixing portion of the flexible tube to be peristaltic together; and
a press means having a leading end that is in contact with the connection portion so that the connection portion is maintained out of an attachment position until a press projection portion of a cover of the peristaltic pump is moved into a closed position moving the connection portion to the attachment position.

* * * * *